(12) United States Patent
Adourian et al.

(10) Patent No.: US 9,274,126 B2
(45) Date of Patent: Mar. 1, 2016

(54) RISK FACTORS AND PREDICTION OF MYOCARDIAL INFARCTION

(75) Inventors: Aram S. Adourian, Concord, MA (US); Yu Guo, Lunenburg, MA (US); Xiaohong Li, Acton, MA (US); Pieter Muntendam, Boxford, MA (US)

(73) Assignee: BG Medicine, Inc., Waltham, MA (US)

( * ) Notice: Subject to any disclaimer, the term of this patent is extended or adjusted under 35 U.S.C. 154(b) by 562 days.

(21) Appl. No.: 12/946,470

(22) Filed: Nov. 15, 2010

(65) Prior Publication Data

US 2011/0137131 A1 Jun. 9, 2011

Related U.S. Application Data

(60) Provisional application No. 61/261,155, filed on Nov. 13, 2009.

(51) Int. Cl.
*G01N 33/68* (2006.01)
*A61B 5/00* (2006.01)

(52) U.S. Cl.
CPC ...... *G01N 33/6893* (2013.01); *G01N 2800/324* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,701,417 A | 10/1987 | Portenhauser et al. |
| 4,945,040 A | 7/1990 | Fless et al. |
| 5,786,163 A | 7/1998 | Hall |
| 6,040,147 A | 3/2000 | Ridker et al. |
| 6,107,045 A | 8/2000 | Koren et al. |
| 6,309,888 B1 | 10/2001 | Holvoet et al. |
| 6,897,030 B2 | 5/2005 | Seilhamer et al. |
| 7,030,152 B1 | 4/2006 | Ridker et al. |
| 7,098,036 B2 | 8/2006 | Koren et al. |
| 7,166,469 B2 | 1/2007 | Holvoet et al. |
| 7,226,729 B1 | 6/2007 | Shimizu et al. |
| 7,341,838 B2 | 3/2008 | Buechler et al. |
| 7,358,055 B2 | 4/2008 | Valkirs et al. |
| 7,361,473 B2 | 4/2008 | Valkirs et al. |
| 7,427,490 B2 | 9/2008 | Valkirs et al. |
| 7,432,107 B2 | 10/2008 | Spanuth |
| 7,482,174 B2 | 1/2009 | Kiefer et al. |
| 7,524,635 B2 | 4/2009 | Buechler |
| 7,527,939 B2 | 5/2009 | Davey et al. |
| 7,534,582 B2 | 5/2009 | Shimizu et al. |
| 7,604,952 B2 | 10/2009 | Holvoet et al. |
| 7,608,418 B2 | 10/2009 | Hess et al. |
| 7,632,647 B2 | 12/2009 | Dahlen et al. |
| 7,655,416 B2 | 2/2010 | Hess et al. |
| 7,732,214 B2 | 6/2010 | Hess et al. |
| 7,749,729 B2 | 7/2010 | Heinecke et al. |
| 7,767,401 B2 | 8/2010 | Lescuyer et al. |
| 7,781,219 B2 | 8/2010 | Hazen et al. |
| 7,790,397 B2 | 9/2010 | Hamm et al. |
| 7,807,380 B2 | 10/2010 | Borgya et al. |
| 7,811,770 B2 | 10/2010 | Borgya et al. |
| 7,820,373 B2 | 10/2010 | Hess et al. |
| 7,867,719 B2 | 1/2011 | Cooke et al. |
| 7,883,854 B2 | 2/2011 | Böger et al. |
| 7,892,844 B2 | 2/2011 | Hess et al. |
| 7,927,812 B2 | 4/2011 | Hess et al. |
| 7,939,287 B2 | 5/2011 | Tsimikas et al. |
| 7,960,123 B2 | 6/2011 | Hess et al. |
| 7,964,614 B2 | 6/2011 | Ridker et al. |
| 7,972,794 B2 | 7/2011 | Caulfield |
| 7,985,560 B2 | 7/2011 | Valkirs et al. |
| 7,998,683 B2 | 8/2011 | Snider et al. |
| 7,998,743 B2 | 8/2011 | Fung et al. |
| 8,003,396 B2 | 8/2011 | Hess et al. |
| 8,053,204 B2 | 11/2011 | Cooke et al. |
| 8,062,896 B2 | 11/2011 | Spanuth |
| 8,114,613 B2 | 2/2012 | Caulfield |
| 8,124,415 B2 | 2/2012 | Liu et al. |
| 2007/0003981 A1 | 1/2007 | Chandler et al. |
| 2007/0099239 A1 | 5/2007 | Tabibiazar et al. |
| 2008/0057590 A1* | 3/2008 | Urdea et al. ............ 436/71 |
| 2008/0300797 A1 | 12/2008 | Tabibiazar et al. |
| 2009/0191647 A1 | 7/2009 | Boga |
| 2009/0209047 A1 | 8/2009 | Kiernan et al. |
| 2009/0274709 A1 | 11/2009 | Xu et al. |
| 2011/0045514 A1 | 2/2011 | Muntendam et al. |

FOREIGN PATENT DOCUMENTS

| | | |
|---|---|---|
| CN | 1167919 A | 12/1997 |
| WO | 01/15744 | 3/2001 |
| WO | 02/083913 | 10/2002 |
| WO | 03/016910 A1 | 2/2003 |
| WO | 2007/124439 A2 | 11/2007 |
| WO | 2008/017928 | 2/2008 |
| WO | 2009/049189 A3 | 4/2009 |
| WO | 2009/111033 | 9/2009 |

OTHER PUBLICATIONS

Klipstein-Grobusch, K. et al. "Serum ferritin and risk of myocardial infarction in the elderly: the Rotterdam Study," Am J Clin Nutr. 1999; 69(6):1231-1236.*
Abe et al., "Transient rise in serum interleukin-8 concentration during acute myocardial infarction," Br. Heart J., 70(2):132-4, Aug. 1993.
Aukrust et al., "Enhanced levels of suluble and membrane-bound CD40 ligand in patients with unstable angina. Possible reflection of T lymphocyte and platelet involvement in the pathogenesis of acute coronary syndromes," Circulation, 100(6):614-20, Aug. 1999.
Bruce, "The place of transaminase in the diagnosis of acute myocardial infarction," J. Coll. Gen. Pract., 6:613-25, Nov. 1963.

(Continued)

*Primary Examiner* — Yelena G Gakh
*Assistant Examiner* — Michelle Adams
(74) *Attorney, Agent, or Firm* — Burns & Levinson LLP

(57) ABSTRACT

Biomarkers and methods are disclosed for diagnosing the risk of a myocardial infarction in an individual by measuring the levels of a set of biomarkers in a sample from an individual. A risk score is calculated for the individual by weighting the measured levels of the biomarkers. The risk score then is used to identify whether the individual is likely to experience a myocardial infarction. In addition, kits are disclosed that include a set of reagents for specifically measuring biomarker levels in a sample from an individual.

28 Claims, 10 Drawing Sheets

OTHER PUBLICATIONS

Chapman, "Relation of cardiac complications to SGOT level in acute myocaridal infarction," Br. Heart J., 34(9):890-6, Sep. 1972.

Faggiano et al., "Serum levels of different tumour markers in patient with chronic heart failure," European Journal of Heart Failure, 7(1):57-61, Jan. 2005.

Gidron et al., "Effect of myocardial infarction on components of fibrinolytic system," Br. Heart J., 39(1):19-24, Jan. 1977.

Gilutz et al., "Alpha 1-antitrypsin in acute myocardial infarction," Br. Heart J., 49(1):26-9, Jan. 1983.

Jansson et al., "von Willebrand factor in plasma: a novel risk factor for recurrent myocardial infarction and death," Br. Heart J., 66(5):351-5, Nov. 1991.

Jovin et al., "High titers of CA-125 may be associated with recurrent ischemic strokes in patients with cancer," Neurology, 64(11):1944-5, Jun. 2005.

Kistorp et al., "N-Terminal Pro-Brain Natriuretic Peptide, C-Reactive Protein, and Urinary Albumin Levels as Predictors of Mortality and Cardiovascular Events in Older Adults," The Journal of American Medical Association, 293(13):1609-1616, Apr. 2005.

Kouris et al., "Clinical and prognostic value of elevated CA125 levels in patients with congestive heart failure," Hellenic J. Cardiol., 47(5):269-74, Sep.-Oct. 2006.

Makin et al., "Assessment of endothelial damage in atherosclerotic vascular disease by quantification of circulating endothelial cells. Relationship with von Willebrand factor and tissue factor," Eur. Heart J., 25(5):371-6, Mar. 2004.

Mitchell et al., "Multimarker Panel to Rule Out Acute Coronary Syndromes in Low-risk Patients," Academic Emergency Medicine 200607 US, 13(7):803-6, Jul. 2006.

Miyao et al., "Role of cytokines and adhesion molecules in ischemia and reperfusion in patients with acute myocardial infarction," Jpn Circ. J., 63(5):362-6, May 1999.

Mohideen, "Brain natriuretic peptide is more than a marker," Ceylon Medical Journal, 47(3):81-2, Sep. 2002.

Moons et al., "Tissue factor and coronary artery disease," Cardiovasc. Res., 53(2):313-25, Feb. 2002.

Morange et al., "Endothelial cell markers and the risk of coronary heart disease: the Prospective Epidemiological Study of Myocardial Infarction (PRIME) study," Circulation, 109(11):1343-8, Mar. 2004 (Epub Mar. 15, 2004).

Nishiyama et al., "Simultaneous elevation of the levels of circulating monocyte chemoattractant protein-1 and tissue factor in acute coronary syndromes." Jpn Circ. J., 62(9):710-2, Sep. 1998.

Nordestgaard et al., "Abstract 1637: Risk Factors and Prediction of Near-Term Myocardial Infarction in Apparently Healthy Men and Women," Circulation, 120(18):S536, Nov. 2009.

Nunez et al., "Carbohydrate antigen 125: an emerging prognostic risk factor in acute heart failure?" Heart, 93(6):716-21, Jun. 2007.

Schönbeck et al., "Soluble CD40L and cardiovascular risk in women," Circulation, 104(19):2266-8, Nov. 2001.

Todor et al., "Identification of a serum gelatinase associated with the occurrence of cerebral aneurysms as pro-matrix metalloproteinase-2," Stroke, 29(8):1580-3, Aug. 1998.

Vasan, "Biomarkers of cardiovascular disease: molecular basis and practical considerations," Circulation, 113(19):2335-62, May 2006.

Volk et al., "The clot-density method of determination of fibrinogen in acute myocardial infarction," Bull. NY Acad. Med., 32(3):244-6, Mar. 1956.

Wilensky et al., "Inhibition of lipoprotein-associated phospholipase A2 reduces complex coronary atherosclerotic plaque development," Nat. Med., 14(10):1059-66, Oct. 2008.

Wilson et al., "Gluthathione S-transferase M1 null genotype is associated with a decreased risk of myocardial infarction," FASEB J., 14(5):791-6, Apr. 2000.

Baber et al., "Thrombolysis in Myocardial Infarction (TIMI) Risk Score and Mortality in Patients With Advanced Chronic Kidney Disease and on Dialysis," American Journal of Cardiology, 103(11):1513-1517, Jun. 2009.

Baptista et al., "Abstract 3800: Predicting Post-infarct Heart Failure: Forget TIMI, Forget GRACE, All You Need is C2ASH?," Jan. 2009, retrieved from the internet: URL:http://circ.ahajournals.org/cgi/content/meeting_abstract/120/18_MeetingAbstracts/S862-b (retrieved on Jan. 7, 2013).

Clayton, "Risk score for predicting death, myocardial infarction, and stroke in patients with stable angina, based on a large randomized trial cohort of patients," BMJ, 331(7521) 5 pages, Oct. 2005.

Foussas et al., "Early Prognostic Usefulness of C-Reative Protein Added to the Thrombolysis in Myocardial Infarction Risk Score in Acute Coronary Syndromes," The American Journal of Cardiology, 96(4)533-537, Aug. 2005.

Beckman et al., "Comparison of Usefulness of Inflammatory Markers in Patients with Versus Without Peripheral Arterial Disease in Predicting Adverse Cardiovascular Outcomes (Myocardial Infarction, Stroke, and Death)," American Journal of Cardiology, 96(10):1374-1378, 2005.

Yalta et al., "Evaluation of Tumor Markers CA-125 and CEA in Acute Myocardial Infarction,"Advances in Therapy, 23(6):1052-1059, Nov./Dec. 2006.

Craig et al., "Plasma Proteins," published Jun. 1, 2000.

Rader et al., "Quantination of Plasma Apolipoproteins in the Primary and Secondary Prevention of Coronary Artery Disease," Annuals of Internal Medicine, 120(12):1012-1025, 1994.

\* cited by examiner

FIG. 1

| Putative biomarker | Quintile of Plasma Level | | | | | P for Model^ | P for Trend |
|---|---|---|---|---|---|---|---|
| | 1 | 2 | 3 | 4 | 5 | | |
| | Odds Ratio (95 percent confidence interval) | | | | | | |
| C-reactive protein | | | | | | | |
| Quintile Value (mg/L) | <0.706 | 0.706-1.266 | 1.267-2.120 | 2.121-4.260 | >4.260 | | |
| Univariable Model | 1.0 | 1.91 (1.01-3.63) | 2.76 (1.47-5.20) | 3.09 (1.69-5.64) | 4.46 (2.45-8.13) | <0.001 | <0.001 |
| Multivariable Model† | 1.0 | 1.17 (0.58-2.37) | 1.82 (0.91-3.66) | 2.06 (1.06-3.99) | 2.67 (1.35-5.28) | 0.014 | 0.010 |
| Alpha-1 antitrypsin | | | | | | | |
| Quintile Value (μmol/L) | <20.0 | 20.0-22.2 | 22.3-24.2 | 24.3-26.8 | >26.8 | | |
| Univariable Model | 1.0 | 2.08 (1.16-3.71) | 1.86 (1.03-3.35) | 2.37 (1.34-4.19) | 3.32 (1.89-5.86) | 0.001 | <0.001 |
| Multivariable Model | 1.0 | 2.40 (1.28-4.50) | 1.79 (0.93-3.47) | 2.28 (1.22-4.27) | 2.85 (1.51-5.41) | 0.010 | 0.004 |
| Fibrinogen | | | | | | | |
| Quintile Value (μmol/L) | <10.3 | 10.3-11.5 | 11.6-13.0 | 13.1-14.9 | >14.9 | | |
| Univariable Model | 1.0 | 1.01 (0.57-1.78) | 1.77 (1.01-3.11) | 1.61 (0.92-2.79) | 2.67 (1.56-4.58) | 0.001 | <0.001 |
| Multivariable Model | 1.0 | 0.92 (0.49-1.74) | 1.52 (0.82-2.81) | 1.48 (0.79-2.75) | 2.11 (1.16-3.85) | 0.040 | 0.006 |
| Transferrin saturation | | | | | | | |
| Quintile Value (%) | <25 | 25-28 | 29-31 | 31-34 | >34 | | |
| Univariable Model | 1.0 | 0.62 (0.39-1.00) | 0.74 (0.46-1.19) | 0.68 (0.42-1.10) | 0.38 (0.22-0.66) | 0.011 | 0.001 |
| Multivariable Model | 1.0 | 0.73 (0.43-1.24) | 0.80 (0.47-1.37) | 0.75 (0.44-1.28) | 0.41 (0.22-0.76) | 0.071 | 0.006 |
| Apolipoprotein A1 | | | | | | | |
| Quintile Value (mg/dL) | <132.9 | 132.9-146.3 | 146.4-159.9 | 160.0-178.0 | >178.0 | | |
| Univariable Model | 1.0 | 0.63 (0.40-1.01) | 0.61 (0.37-0.99) | 0.47 (0.28-0.78) | 0.40 (0.24-0.68) | 0.005 | 0.001 |
| Multivariable Model | 1.0 | 0.52 (0.30-0.90) | 0.60 (0.33-1.12) | 0.49 (0.19-0.82) | 0.39 (0.18-0.85) | 0.066 | 0.049 |
| Iron | | | | | | | |
| Quintile Value (μmol/L) | <12 | 12-13 | 14-16 | 17-19 | >19 | | |
| Univariable Model | 1.0 | 0.69 (0.43-1.11) | 0.76 (0.48-1.19) | 0.65 (0.41-1.07) | 0.41 (0.22-0.74) | 0.046 | 0.003 |
| Multivariable Model | 1.0 | 0.71 (0.41-1.22) | 0.72 (0.43-1.20) | 0.64 (0.37-1.11) | 0.33 (0.17-0.66) | 0.030 | 0.002 |
| Creatinine | | | | | | | |
| Quintile Value (μmol/L) | <75 | 75-81 | 82-87 | 88-95 | >95 | | |
| Univariable Model | 1.0 | 0.95 (0.57-1.58) | 0.65 (0.36-1.18) | 0.99 (0.57-1.69) | 2.31 (1.38-3.86) | <0.001 | <0.001 |
| Multivariable Model | 1.0 | 0.88 (0.50-1.53) | 0.69 (0.35-1.31) | 1.03 (0.57-1.89) | 2.12 (1.18-3.82) | 0.012 | <0.001 |

FIG. 2

| | lymphocyte count | fibrinogen | creatinine | GGT | alkaline phosphatase | iron | apob | apoa1 | apoe | transferrin | alpha-1 antitrypsin | c3 | hsCRP | neutrophil/lymphocyte | transferrin_saturation | apob:apoa1 ratio | total cholesterol | HDL-C | LDL-C | triglycerides | BMI |
|---|---|---|---|---|---|---|---|---|---|---|---|---|---|---|---|---|---|---|---|---|---|
| neutrophil count | 0.18 | 0.19 | 0.02 | 0.08 | 0.13 | -0.08 | -0.01 | 0.03 | 0.05 | 0.03 | 0.21 | 0.17 | 0.23 | 0.56 | -0.08 | -0.04 | -0.01 | 0.08 | -0.04 | 0.02 | -0.02 |
| lymphocyte count | 1 | 0.02 | -0.08 | 0.09 | 0.07 | 0.02 | 0.10 | -0.01 | 0.04 | 0.09 | -0.05 | 0.14 | 0.09 | -0.67 | -0.02 | 0.05 | 0.00 | -0.10 | -0.02 | 0.15 | -0.02 |
| fibrinogen | | 1 | -0.11 | -0.01 | 0.20 | -0.22 | 0.01 | -0.11 | 0.04 | 0.06 | 0.31 | 0.28 | 0.39 | 0.13 | -0.24 | 0.07 | -0.03 | -0.07 | 0.00 | -0.03 | 0.09 |
| creatinine | | | 1 | 0.05 | 0.02 | 0.01 | 0.19 | -0.18 | -0.03 | -0.12 | -0.18 | -0.05 | -0.03 | -0.09 | 0.05 | 0.23 | 0.16 | -0.17 | 0.14 | 0.14 | 0.09 |
| GGT | | | | 1 | 0.15 | 0.16 | 0.15 | 0.02 | 0.15 | 0.09 | -0.01 | 0.20 | 0.24 | 0.09 | 0.08 | 0.12 | 0.02 | -0.09 | -0.09 | 0.21 | 0.09 |
| alk phos | | | | | 1 | -0.16 | 0.09 | -0.04 | 0.07 | 0.16 | 0.09 | 0.24 | 0.23 | 0.04 | -0.18 | 0.10 | 0.01 | -0.04 | 0.03 | 0.09 | 0.12 |
| iron | | | | | | 1 | 0.08 | 0.03 | 0.02 | -0.03 | -0.20 | -0.07 | -0.18 | -0.03 | 0.86 | 0.04 | 0.07 | -0.02 | 0.02 | 0.11 | 0.02 |
| apob | | | | | | | 1 | 0.00 | 0.44 | 0.23 | -0.07 | 0.36 | 0.17 | -0.02 | -0.04 | 0.84 | 0.78 | -0.34 | 0.72 | 0.66 | 0.28 |
| apoa1 | | | | | | | | 1 | 0.27 | 0.18 | 0.04 | 0.03 | -0.13 | 0.04 | -0.03 | -0.49 | 0.35 | 0.73 | -0.01 | -0.04 | -0.16 |
| apoe | | | | | | | | | 1 | 0.15 | 0.03 | 0.18 | 0.16 | 0.09 | -0.06 | 0.25 | 0.42 | 0.04 | 0.21 | 0.39 | 0.08 |
| transferrin | | | | | | | | | | 1 | 0.09 | 0.36 | 0.02 | -0.09 | -0.49 | 0.10 | 0.19 | 0.03 | 0.15 | 0.17 | 0.13 |
| alpha-1 antitrypsin | | | | | | | | | | | 1 | 0.19 | 0.28 | 0.19 | -0.21 | 0.29 | -0.02 | -0.03 | 0.02 | -0.06 | -0.06 |
| c3 | | | | | | | | | | | | 1 | 0.52 | 0.02 | -0.24 | 0.22 | 0.13 | -0.25 | 0.18 | 0.32 | 0.43 |
| hsCRP | | | | | | | | | | | | | 1 | 0.12 | 0.17 | -0.05 | 0.01 | -0.19 | 0.04 | 0.23 | 0.30 |
| neutrophil/lymphocyte | | | | | | | | | | | | | | 1 | -0.05 | -0.08 | -0.02 | 0.16 | -0.01 | -0.09 | -0.04 |
| transferrin_saturation | | | | | | | | | | | | | | | 1 | -0.02 | -0.03 | -0.02 | -0.04 | 0.01 | -0.02 |
| apob:apoa1 ratio | | | | | | | | | | | | | | | | 1 | 0.45 | -0.68 | 0.69 | 0.59 | 0.31 |
| total cholesterol | | | | | | | | | | | | | | | | | 1 | 0.13 | 0.83 | 0.29 | 0.03 |
| HDL-C | | | | | | | | | | | | | | | | | | 1 | -0.17 | -0.45 | -0.31 |
| LDL-C | | | | | | | | | | | | | | | | | | | 1 | 0.17 | 0.08 |
| triglycerides | | | | | | | | | | | | | | | | | | | | 1 | 0.33 |

RISK FACTORS AND PREDICTION OF MYOCARDIAL INFARCTION

REFERENCE TO RELATED APPLICATIONS

This application claims priority to and the benefit of U.S. provisional application No. 61/261,155, filed on Nov. 13, 2009, the entire contents of which are hereby incorporated by reference herein.

BACKGROUND

Myocardial infarction (MI), commonly known as heart attack, is associated with modifiable risk factors but nonetheless remains a leading cause of death and severe disability worldwide. (Yusuf S, Hawken S, Ounpuu S, et al. Effect of potentially modifiable risk factors associated with MI in 52 countries (the INTERHEART study): case-control study. *Lancet.* 364:937-52 (2004)). Toward prevention, contemporary American and European guidelines recommend an integrated two-step approach in which risk assessment (prediction) is followed by individualized risk reduction (therapy), if needed; the higher the risk, the more aggressive the prescribed preventive care. (Third Report of the National Cholesterol Education Program (NCEP) Expert Panel on Detection, Evaluation, and Treatment of High Blood Cholesterol in Adults (Adult Treatment Panel III) final report. *Circulation* 106:3143-421 (2002); European guidelines on cardiovascular disease prevention in clinical practice: executive summary. *Eur. Heart J.* 28:2375-414 (2007)).

Risk assessment in primary prevention of MI has not changed dramatically in the last 40 years. It remains based upon the risk factor concept introduced by the Framingham Heart Study in the 1960's. (Kannel W B, Dawber T R, Kagan A, Revotskie N, Stokes J, 3rd. Factors of risk in the development of coronary heart disease—six year follow-up experience. The Framingham Study. *Ann. Intern. Med.* 55:33-50 (1961)). Because individual risk factors such as plasma cholesterol and blood pressure have low independent predictive ability (Ware J H. The limitations of risk factors as prognostic tools. *N. Engl. J. Med.* 355:2615-7 (2006)), they have been combined to generate global risk assessment measures such as the Framingham Risk Score (FRS) and the European SCORE (Systematic Coronary Risk Evaluation). (Third Report of the National Cholesterol Education Program (NCEP) Expert Panel on Detection, Evaluation, and Treatment of High Blood Cholesterol in Adults (Adult Treatment Panel III) final report. *Circulation* 106:3143-421 (2002); European guidelines on cardiovascular disease prevention in clinical practice: executive summary. *Eur. Heart J.* 28:2375-414 (2007)).

These multivariable risk prediction models provide estimates of 10-year absolute risk and relative risk. The absolute risk is used primarily to assess the need for pharmacological risk reduction, whereas the relative risk is more useful in identifying younger individuals for lifestyle modification to reduce their otherwise high lifetime risk.

Although this two-step preventive approach is sound, it is far from perfect in its present form because established risk factors have limited predictive power even when combined (Wald N J, Morris J K, Rish S. The efficacy of combining several risk factors as a screening test. *J. Med. Screen.* 12:197-201 (2005)), and progression of subclinical disease to clinical MI events still occurs despite initiation of the recommended "optimal" therapy. (Koenig W. Treating residual cardiovascular risk: will lipoprotein-associated phospholipase A2 inhibition live up to its promise? *J. Am. Coll. Cardiol.* 51:1642-4 (2008)). Most MI events occur in individuals classified in FRS/SCORE low and intermediate risk categories, i.e., among misclassified individuals. Further, a substantial residual risk persists even with the best available medical therapy. (Koenig W. Treating residual cardiovascular risk: will lipoprotein-associated phospholipase A2 inhibition live up to its promise? *J. Am. Coll. Cardiol.* 51:1642-4 (2008); Naghavi M, Falk E, Hecht H S, et al. From vulnerable plaque to vulnerable patient—Part III: Executive summary of the Screening for Heart Attack Prevention and Education (SHAPE) Task Force report. *Am. J. Cardiol.* 98:2 H-15H (2006); Lauer M S. Primary prevention of atherosclerotic cardiovascular disease: the high public burden of low individual risk. *JAMA.* 297:1376-8 (2007)).

Thus, there is a need to improve both the detection and the treatment of individuals at highest risk for a MI event.

SUMMARY

Sets of biomarkers have been discovered that are predictive of the risk that an individual will experience a MI, or a heart attack, in the future. In particular, the sets of biomarkers identified herein provide superior discriminatory power as compared to traditional clinical risk factors (e.g., age, smoking status, and cholesterol levels), for predicting whether an individual will experience a MI. More specifically, in various embodiments of the present teachings, the set of biomarkers includes carcinoembryonic antigen and beta-2 microglobulin. In certain embodiments, the biomarker set further includes at least one of N-terminal pro B-type natriuretic peptide, alpha-1 antitrypsin, and C-reactive protein. In addition, kits are provided for measuring one or more biomarkers identified herein to predict the likelihood that an individual will experience a MI.

Thus, in various embodiments, a method for diagnosing the risk of a MI in an individual generally includes measuring the levels of a set of biomarkers in a sample from an individual; calculating a risk score for the individual such as by weighting the measured levels of the biomarkers; and using the risk score to identify a likelihood that the individual will experience a myocardial infarction. The sample can include blood and the individual can be a human. The methods can include transmitting, displaying, storing, or printing; or outputting to a user interface device, a computer readable storage medium, a local computer system or a remote computer system, information related to the likelihood of myocardial infarction in the individual. Various features and steps of the methods of the present teachings can be carried out with or assisted by a suitably programmed computer, specifically designed and/or structured to do so.

In the methods of the present teachings, the levels of biomarkers can be determined by a variety of techniques known in the art, for example, by at least one of an immunoassay, a colorimetric assay, a turbidimetric assay, and flow cytometry. Of course the specific technique used will depend, in part, on the nature of the biomarker to be measured.

In certain embodiments of the present teachings, calculating a risk score includes transforming logarithmically the measured levels of the biomarkers to generate a transformed value for each measured biomarker; multiplying the transformed value of each biomarker by a biomarker constant to generate a multiplied value for each biomarker; and summing the multiplied value of each biomarker to generate the risk score. A risk score can be compared to a standard or reference risk score. A reference risk score can be a standard or a threshold.

The identified biomarkers (i.e., those biomarkers included in the sets of biomarkers according to the present teachings) broadly include alkaline phosphatase, alpha-1 antitrypsin, alpha-fetoprotein, apolipoprotein A1, apolipoprotein B, apolipoprotein E, beta-2 microglobulin, carcinoembryonic antigen, complement component 3, creatinine, fibrinogen, gamma-glutamyl transpeptidase, C-reactive protein (which includes high sensitivity C-reactive protein), iron, lymphocyte count, neutrophil count, N-terminal pro B-type natriuretic peptide (which includes B-type natriuretic peptide), transferrin saturation, and vascular endothelial growth factor A. Any combination of two or more of these biomarkers can be used in accordance with the present teachings. For example, a biomarker set can comprise at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or at least nineteen of these biomarkers.

In certain embodiments, the methods use a set of biomarkers that includes three biomarkers. Examples of sets of biomarkers that include three biomarkers are carcinoembryonic antigen, beta-2 microglobulin, and alpha-1 antitrypsin; carcinoembryonic antigen, beta-2 microglobulin, and C-reactive protein; and carcinoembryonic antigen, beta-2 microglobulin, and N-terminal pro B-type natriuretic peptide.

Where the set of biomarkers includes the three biomarkers carcinoembryonic antigen, beta-2 microglobulin and alpha-1 antitrypsin, various embodiments of the methods of the present teachings use a set of biomarkers that includes biomarkers in addition to those three biomarkers. For example, certain embodiments use a set of four biomarkers that further includes N-terminal pro B-type natriuretic peptide; some embodiments use a set of five biomarkers that further includes apolipoprotein A1 and apolipoprotein B; particular embodiments use a set of seven biomarkers that further includes apolipoprotein A1, apolipoprotein B, alpha-fetoprotein, and transferrin; and various embodiments use a set of eight biomarkers that further includes apolipoprotein A1, apolipoprotein B, alpha-fetoprotein, transferrin, and vascular endothelial growth factor A.

Where the set of biomarkers includes the three biomarkers carcinoembryonic antigen, beta-2 microglobulin, and C-reactive protein, various embodiments of the methods of the present teachings use a set of six biomarkers that further includes apolipoprotein A1, apolipoprotein B, and N-terminal pro B-type natriuretic peptide, in addition to the three listed directly above.

In particular embodiments, the methods use a set of biomarkers that includes seven biomarkers, i.e., alpha-1 antitrypsin, C-reactive protein, apolipoprotein A1, apolipoprotein B, creatinine, alkaline phosphatase, and transferrin saturation. Relatedly, various embodiments of the methods of the present teachings use a set of 13 biomarkers that further includes apolipoprotein E, fibrinogen, gamma glutamyl transpeptidase, complement C3, neutrophil count, and lymphocyte count, in addition to the seven listed directly above.

In another aspect, kits are provided for diagnosing the risk of a MI in an individual. The kit can include a set of reagents that specifically measures the levels of a set of biomarkers in a sample from an individual, and instructions for using the kit for diagnosing the risk of myocardial infarction. In some embodiments, the reagents measure protein levels.

BRIEF DESCRIPTION OF DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 1 is a table showing odds ratios of during four-year of follow-up, according to quintile of baseline levels of putative biomarker, in accordance with an illustrative embodiment. Figure legend: *Likelihood-ratio test of statistical model with variable compared to model without variable. †The multivariable model adjusts for total cholesterol, HDL cholesterol, triglycerides, hypertension, smoking status, diabetes, familial history of premature MI, body mass index, and physical activity.

FIG. 2 is a table showing Spearman correlation coefficients between selected risk factors among non-event (control) subjects, in accordance with an illustrative embodiment. Spearman correlation coefficients between selected risk factors among non-event (control) subjects in the present study (N=463). Bold entries indicate P<0.05. GGT denotes gamma-glutamyl transpeptidase, apob apolipoprotein B, apoa1 apolipoprotein A1, apoe apolipoprotein E, cc3 complement C3, hsCRP high-sensitivity C-reactive protein, neutrophil: lymphocyte the ratio of neutrophil count to lymphocyte count, HDL-C high density lipoprotein cholesterol, LDL-C low density lipoprotein cholesterol, BMI body mass index.

DETAILED DESCRIPTION

Figure 3:
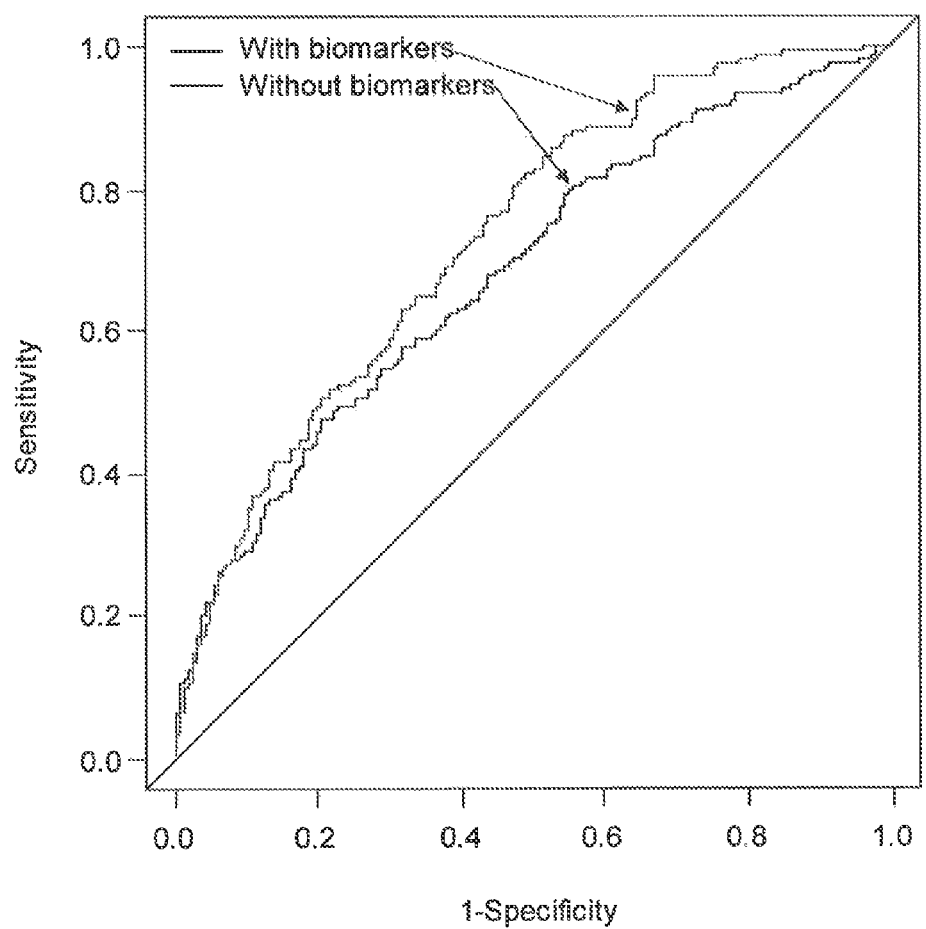
FIG. 3 shows receiver-operating characteristic curves for incident MI based on models of risk that include only established risk factors, and that include established risk factors and 13 putative biomarkers, in accordance with an illustrative embodiment.

Sets of biomarkers have been discovered that are predictive of the risk that an individual will suffer a future myocardial infarction (MI), or a heart attack. A "biomarker" can be any biological feature or variable whose qualitative or quantitative presence, absence, or level in a biological system of an individual, such as a human, is an indicator of a biological state of the system. Accordingly, biomarkers can be useful to assess the health state or status of an individual. For example, multiple biomarker levels can be analyzed using a weighted analysis or algorithm to generate a risk score for an individual. The risk score can be indicative of the likelihood that the individual will suffer a future MI event. In some embodiments, the magnitude of the risk score can be correlated to the level of risk for that individual. For example, a higher risk score can be indicative of a higher likelihood of a future MI event, while a lower risk score can be indicative of a lower likelihood of a future MI event.

As described in detail in the Examples, the present teachings can be used to identify individuals who appear healthy but may be at risk for experiencing a future MI. Armed with this information, individuals at risk can take proactive steps such as exercising, dieting, and/or seeking medical intervention to reduce the likelihood of suffering a MI in the future. Thus, the present teachings can be used more accurately to predict future MI's and possibly save lives. In addition, the present teachings can be used to monitor disease status or disease progression in an individual.

The sets of biomarkers described herein can be useful, alone or in combination with other biomarkers and/or clinical risk factors, to measure the initiation, progression, severity, pathology, aggressiveness, grade, activity, disability, mortality, morbidity, disease sub-classification or other underlying feature of one or more biological processes, pathogenic processes, diseases, or responses to therapeutic intervention in connection with MI. Virtually any biological compound that is present in a sample and that can be isolated from, or measured in, the sample can be used as a biomarker. Non-limiting examples of classes of biomarkers include a polypeptide, a protein, a proteoglycan, a glycoprotein, a lipoprotein, a carbohydrate, a lipid, a nucleic acid, an organic on inorganic chemical, a natural polymer, a metabolite, and a small molecule. A biomarker also can include a physical measurement of the human body, such as blood pressure and cell counts, as well as the ratio or proportion of two or more biological features or variables. In some embodiments, biomarkers from different biological categories can be selected to generate the risk score. Non-limiting examples of different biological categories include inflammation-sensitive plasma proteins, apolipoproteins, markers of iron overload, growth factors, and leukocyte counts.

The "level" or "amount" of a biomarker can be determined by any method known in the art and will depend in part on the nature of the biomarker. For example, the biomarkers levels can be measured by one of more of an immunoassay, a colorimetric assay, a turbidimetric assay, and flow cytometry. It is understood that the amount of the biomarker need not be determined in absolute terms, but can be determined in relative terms. In addition, the amount of the biomarker can be expressed by its concentration in a biological sample, by the concentration of an antibody that binds to the biomarker, or by the functional activity (i.e., binding or enzymatic activity) of the biomarker.

As used herein, "reference" or "control" or "standard" each can refer to an amount of a biomarker in a healthy individual or control population or to a risk score derived from one or more biomarkers in a healthy individual or control population. The amount of a biomarker can be determined from a sample of a healthy individual, or can be determined from samples of a control population.

As used herein, "sample" refers to any biological sample taken from an individual, including blood, blood plasma, blood serum, cerebrospinal fluid, bile acid, saliva, synovial fluid, pleural fluid, pericardial fluid, peritoneal fluid, sweat, feces, nasal fluid, ocular fluid, intracellular fluid, intercellular fluid, lymph urine, tissue, liver cells, epithelial cells, endothelial cells, kidney cells, prostate cells, blood cells, lung cells, brain cells, adipose cells, tumor cells, and mammary cells. The sources of biological sample types may be different subjects; the same subject at different times; the same subject in different states, e.g., prior to drug treatment and after drug treatment; different sexes; different species, for example, a human and a non-human mammal; and various other permutations. Further, a biological sample type may be treated differently prior to evaluation such as using different work-up protocols.

The present teachings generally provide a method for diagnosing the risk of a MI, for example, the near-term risk of a MI, in an individual such as a human or patient. As used herein, "near-term" means within about zero to about six years from a baseline, where baseline is defined as the date on which a sample from an individual is taken for analysis. For example, near-term includes within about one week, about one month, about two months, about three months, about six months, about nine months, about one year, about two years, about three years, about four years, about five years, or about six years from a baseline. As used herein, "near-term risk" means the risk that an individual will experience a MI event within the near-term.

In various embodiments, the methods generally include measuring the levels (or using the measured levels) of a plurality of biomarkers (e.g., a set of biomarkers) in a sample from an individual; calculating a risk score for the individual, such as by weighting the measured levels of the measured biomarkers; and using the risk score to identify a likelihood that the individual will experience a myocardial infarction (e.g., identifying, based on the risk score, a likelihood of a MI event in the individual). In some embodiments, the methods include calculating a risk score, using a suitably programmed computer, based on the measured levels of one or more biomarkers. In certain embodiments, the methods include transmitting, displaying, storing, or printing—or outputting to a user interface device, a computer readable storage medium, a local computer system, or a remote computer system—information related to the likelihood of a MI in the individual.

In various embodiments, the methods use a set of biomarkers, which set includes, but is not limited to: carcinoembryonic antigen, beta-2 microglobulin, and alpha-1 antitrypsin; carcinoembryonic antigen, beta-2 microglobulin, and C-reactive protein; and carcinoembryonic antigen, beta-2 microglobulin, and N-terminal pro B-type natriuretic peptide; carcinoembryonic antigen, beta-2 microglobulin and alpha-1 antitrypsin, and N-terminal pro B-type natriuretic peptide; carcinoembryonic antigen, beta-2 microglobulin and alpha-1 antitrypsin, apolipoprotein A1, and apolipoprotein B; carcinoembryonic antigen, beta-2 microglobulin, alpha-1 antitrypsin, apolipoprotein A1, apolipoprotein B, alpha-fetoprotein, and transferrin; carcinoembryonic antigen, beta-2 microglobulin, alpha-1 antitrypsin, apolipoprotein A1, apolipoprotein B, alpha-fetoprotein, transferrin, and vascular endothelial growth factor A; carcinoembryonic antigen, beta-2 microglobulin, C-reactive protein, apolipoprotein A1, apolipoprotein B, and N-terminal pro B-type natriuretic peptide; alpha-1 antitrypsin, C-reactive protein, apolipoprotein A1, apolipoprotein B, creatinine, alkaline phosphatase, and transferrin saturation; and alpha-1 antitrypsin, C-reactive protein, apolipoprotein A1, apolipoprotein B, creatinine, alkaline phosphatase, transferrin saturation, apolipoprotein E, fibrinogen, gamma glutamyl transpeptidase, complement C3, neutrophil count, and lymphocyte count. In certain embodiments, the set of biomarkers comprises two or more biomarkers selected from alpha-1 antitrypsin, iron, C-reactive protein, creatinine, and fibrinogen. In particular embodiments, the set of biomarkers comprises three or more, four or more, or five of the biomarkers selected from alpha-1 antitrypsin, iron, C-reactive protein, creatinine, and fibrinogen.

The levels of biomarkers can be determined by a variety of techniques known in the art, dependent, in part, on the nature of the biomarker. For example, the level of a biomarker can be determined by at least one of an immunoassay, spectrophotometry, an enzymatic assay, an ultraviolet assay, a kinetic assay, an electrochemical assay, a colorimetric assay, a turbidimetric assay, an atomic absorption assay, and flow cytometry. Other analytical techniques such as mass spectrometry, liquid chromatography such as high performance/pressure liquid chromatography (HPLC), gas chromatography, nuclear magnetic resonance spectrometry, related techniques and combinations and hybrids thereof, for example, a tandem liquid chromatography-mass spectrometry (LC-MS) instrument can be used as appropriate.

In some embodiments, calculating a risk score includes transforming logarithmically the measured levels of the biomarkers to generate a transformed value for each measured biomarker; multiplying the transformed value of each biomarker by a biomarker constant to generate a multiplied value for each biomarker; and summing the multiplied value of each biomarker to generate the risk score. Of course other means known to those skilled in the art can be used to calculate a risk or similar score based on the measured levels of the set of biomarkers, which score can be predictive of a likelihood of an individual experiencing a MI event.

A risk score can be compared to a standard or reference risk score. A reference risk score can be a standard (e.g., a number) or a threshold (e.g., a line on a graph). In certain embodiments, if a risk score is greater than a reference risk score, the individual can have an increased likelihood of experiencing a MI, for example, a future MI event. In some embodiments, if a risk score is less than a reference risk score, the individual can have a decreased likelihood of experiencing a MI, for example, a future MI event. In some embodiments, the magnitude of individual's risk score, or the amount by which it exceeds a reference risk score, can be indicative of or correlated to that individual's level of risk. For example, a higher risk score can be indicative of a higher likelihood of a future MI event, while a lower risk score can be indicative of a lower likelihood of a future MI event. Conversely, if the individual's risk score is below a reference risk score, the individual may not be at significant risk for experiencing a future MI event.

Establishing a reference risk score, standard, threshold, decision boundary, or a "cutoff" score (collectively, a "reference risk score") for a particular set of biomarkers is known in the art. (Szklo, Moyses and Nieto, F. Javier. *Epidemiology: beyond the basics*. Second Edition. Sudbury, MA: Jones and Bartlett Publishers (2007); Schlesselman, James J. *Case-Control Studies*. New York: Oxford University Press (1982); Anderson K M, Odell P M, Wilson P W, Kannel W B. Cardiovascular disease risk profiles. *Am Heart J.* 121:293-8 (1991); Eichler K, Puhan M A, Steurer J, Bachmann L M. Prediction of first coronary events with the Framingham score: a systematic review. *Am Heart J.* 153(5):722-31, 731.e1-8 (2007); Hoffmann U, Massaro J M, Fox C S, Manders E, O'Donnell C J. Defining normal distributions of coronary artery calcium in women and men from the Framingham Heart Study. *Am J. Cardiol.* 102(9):1136-41, 1141.e1. (2008)).

The methods of the present teachings permit not only the diagnosis of a likelihood or a risk of a future MI event, for example, a near-term MI event, but also can include recommending, authorizing, or administering treatment if the individual is identified as having an increased likelihood of a myocardial infarction. In some embodiments of the methods, information related to the likelihood of a MI event of an individual can be transmitted to a person in a medical industry, a medical insurance provider, a health care provider, or to a physician.

Moreover, the same methodology used to identify an individual as being at an increased likelihood of experiencing an MI can be adapted to other uses. For example, a risk score can be used to screen candidate drugs that mitigate the causative factors which lead to MI. In this instance, treatment with candidate drugs can be monitored by monitoring biomarker levels and/or the risk score. Moreover, with any drug that has already been found effective to reduce the likelihood of a future MI, it can be that certain individuals may be responders and some may be non-responders. Accordingly, an individual's risk score could be monitored during treatment to determine if the drug is effective. For example, if the individual's risk score decreases in response to treatment, the individual may be responding to the treatment and therefore also may be at a decreased risk for experiencing a future event. Of course, there may not be any existing, known population of responders and non-responders so that the efficacy of drug treatment with respect to any future MI event in an individual should be and can be monitored over time. To the extent the drug is not efficacious, its use can be discontinued and another drug supplied in its place.

The risk score can be calculated as described herein using a suitably programmed computer, which can include other electronic devices. In addition, that or another suitably programmed computer can compare the risk score to a reference risk score for purposes of determining a likelihood that the individual will experience a MI. Suitable programming can include, for example, software, firmware, or other program code that enables the computer to process, analyze, and/or convert measured biomarker levels into a risk score, and to interpret the likelihood of MI based on the risk score. Such programming can be included within the computer, or can be embodied on a computer readable medium such as a portable computer readable medium. Of course, other steps or processes of the present teachings can be carried out using or can be assisted by a suitably programmed computer, for example, the measuring of the levels of biomarkers, the using of a risk score, the recommending and/or authorizing of treatment, and the transmitting, displaying, storing, printing, and/or outputting of information.

After a risk score and/or a likelihood of a MI is determined, information about the risk score and/or a likelihood of a future MI in an individual can be displayed or outputted to a user interface device, a computer readable storage medium, or a local or remote computer system. Such information can include, for example, the measured levels of one or more biomarkers, the risk score or an equivalent thereof (e.g., a graph, figure, symbol, etc.), and any other data related to the methods described herein. Displaying or outputting information means that the information is communicated to a user using any medium, for example, orally, in writing, on a printout, by visual display computer readable medium, computer system, or other electronic device (e.g., smart phone, personal digital assistant (PDA), laptop, etc.). It will be clear to one skilled in the art that outputting information is not limited to outputting to a user or a linked external component(s), such as a computer system or computer memory, but can alternatively or additionally be outputted to internal components, such as any computer readable medium.

Computer readable media can include, but are not limited to, hard drives, floppy disks, CD-ROMs, DVDs, and DATs. Computer readable media does not include carrier waves or other wave forms for data transmission. It will be clear to one skilled in the art that the various sample evaluation and diagnosis methods disclosed and claimed herein, can, but need not be, computer-implemented, and that, for example, the displaying or outputting step can be done by, for example, by communicating to a person orally or in writing (e.g., in handwriting).

According to various embodiments, at least one of a risk score, a likelihood of a MI, measured biomarker levels, a reference risk score, and equivalents thereof, can be displayed on a screen or a tangible medium. In certain embodiments, such information can be transmitted to a person in a medical industry, a medical insurance provider, a health care provider, or to a physician.

The present teachings also include kits and systems useful for performing the diagnostic methods described herein. The methods described herein can be performed by, for example, diagnostic laboratories, service providers, experimental laboratories, and individuals. The kits can be useful in these settings, among others.

Kits can include reagents and materials for measuring the levels of one or more biomarkers in a sample from an individual, analyzing the measured levels, and identifying whether the individual is at risk for a MI. For example, in some embodiments, the kit can include a needle, syringe, vial, or other apparatus for obtaining and/or containing a sample from an individual. In some embodiments, the kit can include at least one reagent which is used specifically to detect or quantify a biomarker disclosed herein. That is, suitable reagents and techniques readily can be selected by one of skill in the art for inclusion in a kit for detecting or quantifying those biomarkers.

For example, where the biomarker is a protein, the kit can include reagents (e.g., an antibody) appropriate for detecting proteins using, for example, an immunoassay (e.g., chemiluminescent immunoassay), a colorimetric assay, or a turbidimetric assay. Where the biomarker is a cell, the kit can include reagents appropriate for detecting cells using, for example, flow cytometry. Where the biomarker is an organic or inorganic chemical, lipid, or small molecule, the kit can include reagents appropriate for detecting such biomarkers using, for example, HPLC, enzymatic assays, spectrophotometry, ultraviolet assays, kinetic assays, electrochemical assays, colorimetric assays, atomic absorption assays, and mass spectrometry. Where the biomarker is a nucleic acid (e.g., RNA) or a protein encoded by a nucleic acid, the kit can include reagents appropriate for detecting nucleic acids using, for example, PCR, hybridization techniques, and microarrays.

Depending on the biomarkers to be measured, the kit can include: extraction buffers or reagents, amplification buffers or reagents, reaction buffers or reagents, hybridization buffers or reagents, immunodetection buffers or reagents, labeling buffers or reagents, and detection means.

Kits can also include a control, which can be a control sample, a reference sample, an internal standard, or previously generated empirical data. The control may correspond to a normal, healthy individual or an individual having a known MI disease status. In addition, a control may be provided for each biomarker or the control may be a reference risk score.

Kits can include one or more containers for each individual reagent. Kits can further include instructions for performing the methods described herein and/or interpreting the results, in accordance with any regulatory requirements. In addition, software can be included in the kit for analyzing the detected biomarker levels, calculating a risk score, and/or determining a likelihood of MI. Preferably, the kits are packaged in a container suitable for commercial distribution, sale, and/or use.

A system for performing the methods disclosed herein can include the analytical instruments used to measure the levels of a set of biomarkers along with a suitably programmed computer for carrying out one or more steps of the methods. For example, the suitably programmed computer can carry out or assist in one or more of measuring the levels of a set of biomarkers in a sample from an individual; calculating a risk score by the various techniques taught herein or known in the art; using the risk score to indentify a likelihood that an individual will experience a myocardial infarction; and displaying information related to the likelihood of a MI such as the measured biomarker levels, the risk score, the likelihood of a MI, a reference risk score, and equivalents thereof.

The following examples are provided for illustration, not limitation.

EXAMPLE 1

Identification of Putative Biomarkers

Methods
 Study Population
 The purpose of the present study was to improve the detection of individuals at highest risk by focusing on those who develop a MI within four years after risk assessment. Risk factors and predictors of such near-term MI have not been reported before, largely because most studies are too small to accumulate sufficient numbers of near-term MI events. Clearly, risk factors for near-term events like MI dominated by thrombosis superimposed on inflamed and ruptured atherosclerotic plaques could differ from risk factors for longer-term events dominated by slow development of atherosclerosis. For this purpose, a large community-based, prospective, nested case-control study was used, namely, the Copenhagen City Heart Study combined with the Copenhagen General Population Study drawing upon 45,735 men and women.

Participants were from the 2001-2003 examination of the Copenhagen City Heart Study and from the 2003-2007 examination of the Copenhagen General Population Study. The Copenhagen City Heart Study is a prospective cardiovascular population study of the Danish general population initiated in 1976 comprising white men and women of Danish descent attending one or several examinations. (Nordestgaard B G, Benn M, Schnohr P, Tybjaerg-Hansen A. Nonfasting triglycerides and risk of MI, ischemic heart disease, and death in men and women. *JAMA*. 298:299-308 (2007)). During the 2001-2003 examination, blood samples were collected from 5907 individuals (50% participation rate). The Copenhagen General Population Study (CGPS) is a prospective study of the Danish general population initiated in 2003 and still recruiting (Nordestgaard B G, Benn M, Schnohr P, Tybjaerg- Hansen A. Nonfasting triglycerides and risk of MI, ischemic heart disease, and death in men and women. *JAMA.* 298:299-308 (2007); Frikke-Schmidt R, Nordestgaard B G, Stene M C, et al. Association of loss-of-function mutations in the ABCA1 gene with high-density lipoprotein cholesterol levels and risk of ischemic heart disease. *JAMA.* 299:2524-32 (2008)), the aim is to total 100,000 participants ascertained exactly as in The Copenhagen City Heart Study. Between 2003 and 2007, 39,828 individuals from the Copenhagen General Population Study returned blood samples (45% participation rate). Within four years of blood draw in the combined studies, 252 participants with incident nonfatal or fatal MI were identified. Controls were matched to cases from the same study, randomly selected in a 2:1 ratio from participants with a blood sample and without a history of MI (but they could previously have had other cardiovascular diseases or revascularization procedures), and matched for age (within 1 year), gender, year of examination and of blood draw (within 1 year), and HMG-CoA reductase inhibitor use (yes or no).

Information on diagnoses of MI (World Health Organization; International Classification of Diseases, $8^{th}$ edition: codes 410; $10^{th}$ edition: codes I21-I22) was collected and verified by reviewing all hospital admissions and diagnoses entered in the national Danish Patient Registry; medical records from hospitals and general practitioners were used to verify MI diagnoses that required the presence of at least two of the following criteria: characteristic chest pain, elevated cardiac enzymes, and electrocardiographic changes indicative of MI. Five cases were only able to be matched to one control instead of two. A total of 252 cases and 499 controls were thus available for analysis.

These studies were approved by Herlev Hospital and by Danish ethical committees. Participants gave written informed consent.

Established Risk Factors

Nonfasting total cholesterol, high-density lipoprotein (HDL) cholesterol, and triglycerides were measured on fresh plasma. (Boehringer Mannheim, Mannheim, Germany). Low-density lipoprotein (LDL) cholesterol was calculated according to Friedewald if triglycerides were less than 4 mmol/L, but measured directly at higher triglyceride levels. Smoking status was defined as never, past, or current smokers. Diabetes mellitus was self-reported disease, use of insulin or oral hypoglycemic agents, and/or nonfasting plasma glucose greater than 11 mmol/L. Physical inactivity was leisure time activity less than four hours weekly and predominantly sedentary work. Body mass index was weight (kg) divided by height squared ($m^2$). Blood pressure was measured after 5 minutes rest, and with the subject in the sitting position. Family history of premature MI was defined as MI in a male first-degree relative prior to 55 years or MI in female first degree relative prior to 65 years.

Putative Biomarkers

From non-fasting fresh blood samples, 14 biomarkers were measured using colorimetric and turbidimetric assays (Konelab, Helsinki, Finland, Dade Behring, Deerfield, Ill., USA, ILS Laboratories Scandinavia, Allerød, Denmark or Dako, Glostrup, Denmark) or flow cytometry (Bayer, Germany), namely, high sensitivity C-reactive protein (CRP), fibrinogen, alpha-1 antitrypsin, complement component 3 (complement C3), apolipoprotein A1, apolipoprotein B, apolipoprotein E, iron, transferrin (transferrin saturation), creatinine, alkaline phosphatase, gamma-glutamyl transpeptidase, lymphocyte count and neutrophil count. Transferrin saturation (%) was calculated by dividing serum iron level (µmol/L) by twice the transferrin level (µmol/L). As used herein, "high sensitivity C-reactive protein" and "C-reactive protein" (and "CRP") are used interchangeably and refer to the same protein, unless understood otherwise.

Blood samples from the 751 subjects were frozen for subsequent analyses. These frozen blood plasma samples were subsequently thawed for the measurement of additional proteins and other biochemical measures, as follows. The following proteins were measured in each of the 751 blood plasma samples using the HumanMAP version 1.6 Luminex multiplex immunoassay technology by Rules Based Medicine, Inc. (Austin, Tex.): alpha-fetoprotein, beta-2 microglobulin, carcinoembryonic antigen, and vascular endothelial growth factor A. The protein N-terminal pro B-type natriuretic peptide (NT-proBNP) was measured in each of the 751 blood plasma samples using the SearchLight® SearchLight chemiluminescent immunoassay measurement technology (Thermo Scientific, Rockford, Ill.). As used herein, "N-terminal pro B-type natriuretic peptide" and "B-type natriuretic protein" (and "NT-proBNP") are used interchangeably and refer to the same protein, unless understood otherwise.

Statistical Analysis

Variables were compared at baseline between case and control subjects using Student's unpaired t-test for continuous measures and Fisher's exact test for proportions. Baseline is defined as the date of blood draw for each subject. Correlations between variables were calculated using Spearman correlation.

Levels of continuous variables were categorized into quintiles based upon their distribution among control subjects. Conditional logistic regression was used to examine association between baseline variable levels and incidence of MI. Seventeen baseline biomarker variables were evaluated: alpha-1 antitrypsin, alkaline phosphatase, apolipoprotein A1, apolipoprotein B, apolipoprotein E, complement C3, creatinine, fibrinogen, gamma-glutamyl transpeptidase, iron, transferrin, transferrin saturation, C-reactive protein, lymphocyte count, neutrophil count, the ratio of neutrophil count to lymphocyte count, and the ratio of apolipoprotein B to apolipoprotein A1.

Two statistical models were constructed. One model considered the variable under evaluation with no adjustment for other risk factors. A second model was multivariable and adjusted for nine established baseline risk factors of total cholesterol (in quintiles based on control subjects), HDL cholesterol (in quintiles based on control subjects), triglycerides (in quintiles based on control subjects), five blood pressure categories (systolic/diastolic pressure less than 120/80 mmHg, ≥120/80 and <130/85 mmHg, ≥130/85 and <140/90 mmHg, ≥140/90 and <160/100 mmHg, or ≥160/100 mmHg or use of antihypertensive therapy), smoking status (never smoked, current smoker, former smoker), diabetes mellitus (yes/no), family history of premature MI (yes/no), body mass index (treated as a continuous variable) and physical activity (dichotomized, less than four hours of activity per week and sedentary work, or greater than four hours of activity per week and/or non-sedentary work). A distinct statistical model that did not consider any biomarkers and comprised solely the nine established baseline risk factors categorized as described above was also evaluated. The likelihood-ratio test was used to determine whether a logistic regression model that included the variable of interest provided a better fit than did a logistic regression model without the variable. To test for linear trend across categories, median levels within quintiles were used as a continuous measure.

In a separate, secondary analysis, a conditional logistic regression model that included the nine established baseline risk factors enumerated above and 13 of the 17 biomarkers was evaluated, with incident MI as the outcome. Four biomarkers were not included in this analysis due to high correlation with other biomarkers: serum iron and transferrin were removed in favor of transferrin saturation, the ratio of neutrophil count to lymphocyte count was removed and neutrophil count and lymphocyte count were retained individually, and the ratio of apolipoprotein B to apolipoprotein A1 was removed and apolipoprotein B and apolipoprotein A1 were retained individually. Established risk factors were categorized as previously, and biomarker levels for this analysis were log-transformed and considered as continuous variables. The conditional logistic regression model and the associated probability of a MI calculated for each subject were used to construct receiver operating characteristic (ROC) curves, with the binary outcome of occurrence of a MI. As a complement to the area under the ROC curve for assessing improvement in risk model performance, the integrated discrimination improvement, or IDI, statistic, and the relative IDI statistic, were calculated. (AHA Scientific Statement. Criteria for evaluation of novel markers of cardiovascular risk. *Circulation* 119:2408-2416 (2009); Pencina M J, D'Agostino R B Sr, D'Agostino R B Jr, Vasan R S. Evaluating the added predictive ability of a new marker: from area under the ROC curve to reclassification and beyond. *Stat Med*. Jan 30; 27(2):157-72 (2008)) The IDI test is a measure of the performance of a risk prediction model, and is complementary to the area under the ROC curve. The relative IDI is equivalent to the improvement in the difference between the average predicted risk of individuals who developed an event and the average predicted risk of individuals who did not develop an event.

In addition, a "multimarker score" was constructed comprising the log-transformed levels of the 13 biomarkers as follows: multimarker score=$(\beta_1 \times biomarker_1)+(\beta_2 \times biomarker_2)+(\beta_i \times biomarker_i)$ and so on, where $\beta_i$ denotes the estimate of the beta coefficients associated with the $i^{th}$ biomarker in the conditional logistic regression model that also included the nine established risk factors.

Subjects with missing measurements in any of the 17 blood-based biomarker variables of interest or any of the nine established baseline risk factors were excluded. The final dataset for statistical analysis thus consisted of 699 subjects, comprising 236 cases and 463 matched controls.

All P values were two-tailed. Probability values less than 0.05 were considered significant. All confidence intervals were calculated at the 95 percent level. Statistical analyses were conducted with the use of SAS software, version 9.1 (SAS Institute) and R software, version 2.6.

Results

Using the sex-specific risk equations published by the Framingham Heart Study (Wilson P W, D'Agostino R B, Levy D, Belanger A M, Silbershatz H, Kannel W B. Prediction of coronary heart disease using risk factor categories. *Circulation* 97:1837-47 (1998)), the 10-year absolute risk for the entire study population at baseline was calculated. Only 36% of all near-term MI events occurred in those categorized as high risk (Table 1). In other words, 64% of individuals who actually experienced a near-term MI event were not identified as being at high risk.

Risk Factors

Table 1 shows baseline characteristics for the study population, including some of the major cardiovascular risk factors identified in longer-term studies. In a model comprising nine of these established risk factors, HDL cholesterol, smoking status (currently smoking) and presence of diabetes were significantly associated with near-term incident MI (Table 2). Cases and controls were matched on age and gender in the present study, and as such age and gender are not included in the model.

TABLE 1

Baseline characteristics of cases and controls.

| Characteristic | MI Cases (n = 236) | Controls (n = 463) | P* |
|---|---|---|---|
| Age, y | 68.4 (10.9) | 68.4 (10.8) | matched |
| Male, % | 62.3 | 62.3 | matched |
| Smoking status, % | | | |
| Never | 19.5 | 28.3 | 0.01 |
| Past | 41.9 | 47.7 | 0.24 |
| Current | 38.6 | 24.0 | <0.01 |
| Body mass index, kg/m$^2$ | 27.8 (4.9) | 26.6 (4.0) | <0.01 |
| Family history of premature | | | |
| MI, % | 5.9 | 3.8 | 0.25 |
| Diabetes, % | 12.3 | 6.3 | <0.01 |
| Physically inactive, % | 47.0 | 45.4 | 0.69 |
| Blood pressure, mmHg | | | |
| Diastolic | 85.6 (13.1) | 83.7 (11.1) | 0.05 |
| Systolic | 152.5 (21.8) | 147.1 (19.5) | <0.01 |
| Cholesterol, mmol/L | | | |
| Total cholesterol | 5.8 (1.2) | 5.7 (1.1) | 0.21 |
| HDL cholesterol | 1.4 (0.5) | 1.6 (0.6) | <0.01 |
| LDL cholesterol | 3.5 (1.1) | 3.4 (1.1) | 0.04 |
| Triglycerides, mmol/L | 2.04 (1.20) | 1.76 (1.27) | <0.01 |
| Medication use, % | | | |
| Statin | 14.3 | 13.6 | matched |
| Antihypertensive therapy | 39.4 | 29.4 | <0.01 |
| Diuretic therapy | 23.3 | 13.2 | <0.01 |
| 10-year Framingham CVD Risk Category*, % | | | |
| Low | 17.2 | 34.7 | <0.01 |
| Moderate | 46.8 | 39.9 | <0.01 |
| High | 36.0 | 25.4 | <0.01 |

Continuous variables are reported as mean(standard deviation).
*Unadjusted 10-year cardiovascular disease (CVD) risk categories based on LDL-cholesterol categories, after Wilson et al.

TABLE 2

Odds ratios of MI during 4-year of follow-up, for established risk factors.

| Established risk factor | Odds Ratio (95% CI) of highest category* | P for highest category |
|---|---|---|
| Smoking status | | |
| Past | 1.32 (0.83-2.10) | 0.24 |
| Current | 2.96 (1.77-4.95) | <0.01 |
| Body mass index | 1.04 (0.99-1.08) | 0.11 |
| Family history of premature MI | 1.99 (0.88-4.50) | 0.10 |
| Diabetes | 1.82 (0.99-3.23) | 0.05 |
| Physically inactive | 1.03 (0.71-1.50) | 0.86 |
| Blood pressure | 2.58 (0.87-7.62) | 0.09 |
| Total cholesterol | 2.01 (0.82-4.92) | 0.13 |
| HDL cholesterol | 0.29 (0.13-0.64) | <0.01 |
| Triglycerides | 1.22 (0.59-2.52) | 0.60 |

*Odds ratios are from a multivariable model comprising all nine risk factors.

Reported odds ratios for quintiled variables are those corresponding to the highest quintile relative to the lowest quintile (see Methods Section). For smoking, 'never smoked' is the referent. For familial history of premature CHD and diabetes, 'no' is the referent category. For physical inactivity, greater than four hours of activity per week and/or non-sedentary work is the referent category. For blood pressure, the referent category is systolic/diastolic pressure less than 120/80 mmHg. Body mass index is treated as a continuous variable. P-values is for regression coefficient for these categories.

After adjustment for established risk factors, five of seventeen putative biomarkers remained individually associated with four-year risk of MI (based on statistical significance of comparison of highest and lowest quintiles, likelihood-ratio test, and monotonicity of trend across quintiles): odds ratios comparing highest to lowest quintiles were 2.85 (95% CI:1.51-5.41; P=0.001) for $\alpha_1$-antitrypsin, 2.76 (1.35-5.28; p=0.005) for C-reactive protein, 2.12 (1.18-3.82; p=0.01) for creatinine, 2.11 (1.16-3.85, P=0.01) for fibrinogen, and 0.33 (0.17-0.66; P=0.002) for iron (Table 3, FIG. 1). Two other biomarkers, apolipoprotein A1 and transferrin saturation, were statistically significant based on comparison of highest and lowest quintiles.

The odds ratios associated with quintiles of the multimarker score were significant in both unadjusted and adjusted models, with a univariate and multivariate adjusted odds ratios for highest quintile relative to lowest quintile of 11.8 (95% CI:6.00-23.3; P<0.001) and 8.56 (3.91-18.7; P<0.001) (Table 4). This multimarker score consists of a linear combination of the following 13 biomarkers: alpha-1 antitrypsin, alkaline phosphatase, apolipoprotein A1, apolipoprotein B, apolipoprotein E, complement C3, creatinine, fibrinogen, gamma-glutamyl transpeptidase, transferrin saturation, C-reactive protein, lymphocyte count, and neutrophil count.

The levels of C-reactive protein, fibrinogen and $\alpha_1$-antitrypsin showed a moderate degree of correlation with each other, as did C-reactive protein and body mass index (FIG. 2). The levels of a number of other established risk factors and putative biomarkers were also associated.

TABLE 4

Relation Of Multimarker Score To Outcome:Odds Ratios Of MI During 4-Year Of Follow-Up, According To Quintile Of Multimarker Score.

| | Unadjusted Odds Ratio (95% CI) | P† | Adjusted Odds Ratio (95% CI)* | P† |
|---|---|---|---|---|
| Quintile 5 | 11.8 (6.00-23.3) | <0.001 | 8.56 (3.91-18.7) | <0.001 |
| Quintile 4 | 7.37 (3.82-14.2) | <0.001 | 6.19 (3.04-12.6) | <0.001 |
| Quintile 3 | 4.49 (2.31-8.71) | <0.001 | 3.66 (1.79-7.47) | <0.001 |
| Quintile 2 | 2.61 (1.34-5.07) | 0.005 | 2.30 (1.14-4.67) | 0.020 |
| Quintile 1 | 1.0 | — | 1.0 | — |

*Adjusted odds ratios are from a multivariable model comprising the multimarker score (as quintiles), and 9 established risk factors.
†P value for quintile compared to lowest quintile.

The multimarker score comprises measurements of the following 13 biomarkers: alpha-1 antitrypsin, alkaline phosphatase, apolipoprotein A1, apolipoprotein B, apolipoprotein E, complement C3, creatinine, fibrinogen, gamma-glutamyl transpeptidase, transferrin saturation, C-reactive protein, lymphocyte count, and neutrophil count.

Prediction of Risk

Referring to FIG. 3, FIG. 3 shows receiver-operating characteristic curves (ROC) for incident MI based on models of risk that include only established risk factors, and that include established risk factors and 13 putative biomarkers, in accordance with an illustrative embodiment. The included putative biomarkers are alpha-1 antitrypsin, alkaline phosphatase, apolipoprotein A1, apolipoprotein B, apolipoprotein E, complement C3, creatinine, fibrinogen, gamma-glutamyl transpeptidase, transferrin saturation, C-reactive protein, lymphocyte count, and neutrophil count. The area under the ROC curve (95% CI) with only established risk factors and without biomarkers is 0.69 (0.65-0.73), and the area under the

TABLE 3

Putative circulating biomarkers for near-term MI.

| Biomarker | Adjusted Odds Ratio (95% CI) associated with highest category* | P for highest category | Adjusted P for highest category | P for Model** | P for Trend |
|---|---|---|---|---|---|
| Alpha-1 antitrypsin | 2.85 (1.51-5.41) | 0.001 | 0.01 | 0.01 | 0.004 |
| C-reactive protein | 2.67 (1.35-5.28) | 0.005 | 0.02 | 0.01 | 0.01 |
| Creatinine | 2.12 (1.18-3.82) | 0.01 | 0.04 | 0.003 | 0.000 |
| Fibrinogen | 2.11 (1.16-3.85) | 0.01 | 0.04 | 0.04 | 0.006 |
| Iron | 0.33 (0.17-0.66) | 0.002 | 0.01 | 0.03 | 0.002 |
| Apolipoprotein A1 | 0.39 (0.18-0.85) | 0.02 | 0.04 | 0.07 | 0.05 |
| Transferrin saturation | 0.41 (0.22-0.76) | 0.005 | 0.02 | 0.07 | 0.006 |
| ApoB:ApoA1 ratio | 2.04 (0.80-5.22) | 0.14 | 0.22 | 0.29 | 0.15 |
| Apolipoprotein B | 1.68 (0.61-4.67) | 0.32 | 0.42 | 0.86 | 0.38 |
| Neutrophil:lymphocyte ratio | 1.64 (0.90-2.99) | 0.11 | 0.21 | 0.40 | 0.06 |
| Complement C3 | 1.59 (0.84-3.01) | 0.16 | 0.23 | 0.19 | 0.08 |
| Alkaline phosphatase | 1.54 (0.88-2.68) | 0.13 | 0.22 | 0.15 | 0.04 |
| Neutrophil count | 1.28 (0.72-2.27) | 0.41 | 0.50 | 0.23 | 0.43 |
| Transferrin | 1.15 (0.64-2.06) | 0.64 | 0.72 | 0.88 | 0.71 |
| Gamma-glutamyl transpeptidase | 1.13 (0.63-2.02) | 0.68 | 0.72 | 0.63 | 0.27 |
| Apolipoprotein E | 0.92 (0.48-1.75) | 0.80 | 0.80 | 0.75 | 0.98 |
| Lymphocyte count | 0.61 (0.34-1.11) | 0.11 | 0.21 | 0.22 | 0.12 |

*Odds ratios are from a multivariable model also including the 9 established risk factors. Reported odds ratio, P value, and adjusted P value (false discovery rate controlled at 0.20) correspond to comparison of the extreme quintile relative to the reference quintile (see Methods Section).
**Likelihood-ratio test of statistical model with variable compared to model without variable.

ROC curve with established risk factors and biomarkers is 0.74 (0.70-0.78). The area under the ROC curve increased with the addition of multiple biomarkers to the nine established risk factors (FIG. 3), from 0.69 to 0.74 (Table 5); however, this increase did not achieve statistical significance. In contrast, the integrated discrimination improvement test revealed statistically significant improvement with the incorporation of biomarkers to the risk model, reaching a 4.3 percent improvement with incorporation of 13 biomarkers, relative to a model with no biomarkers included (P<0.001). Improvement for individual cases and controls are illustrated in FIG. 4.

Figure 4:
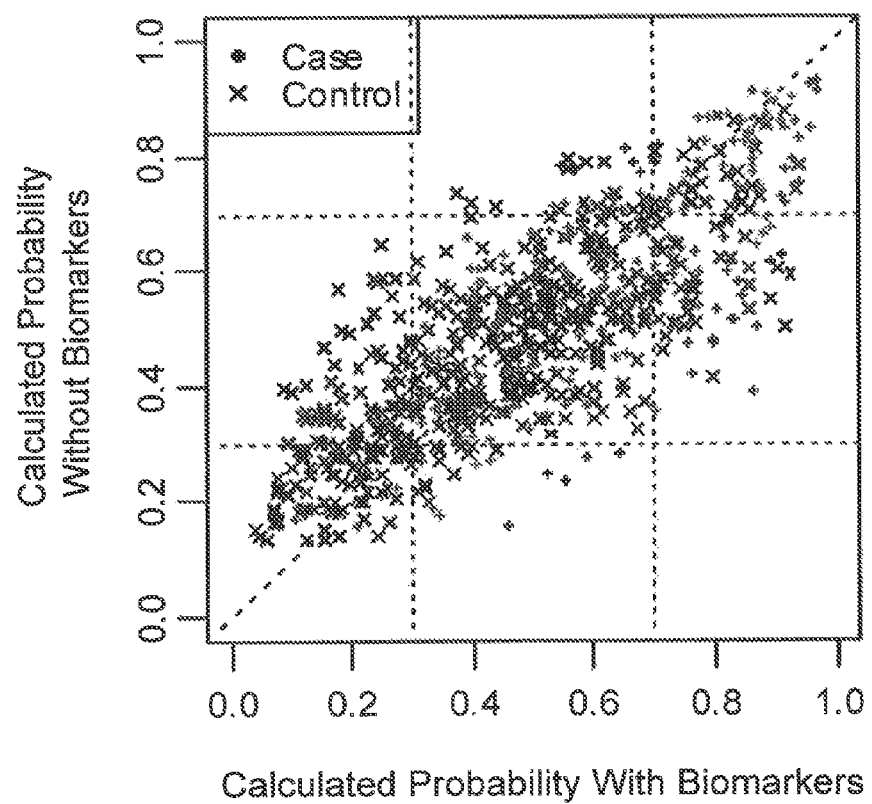
FIG. 4 is a scatter plot of calculated case-control probabilities of near-term MI for each subject, from a model comprising solely established risk factors (left axis) and from a model comprising established risk factors and 13 putative biomarkers (bottom axis), in accordance with an illustrative embodiment.

Referring to FIG. 4, FIG. 4 shows a scatter plot of calculated case-control probabilities of near-term MI for each subject, from a model comprising solely established risk factors (left axis) and from a model comprising established risk factors and 13 putative biomarkers (bottom axis), in accordance with an illustrative embodiment. The established risk factors are total cholesterol, HDL cholesterol, triglycerides, hypertension, smoking status, diabetes, familial history of premature MI, body mass index, and physical activity. The included putative biomarkers are alpha-1 antitrypsin, alkaline phosphatase, apolipoprotein A1, apolipoprotein B, apolipoprotein E, complement C3, creatinine, fibrinogen, gamma-glutamyl transpeptidase, transferrin saturation, C-reactive protein, lymphocyte count, and neutrophil count. The vertical and horizontal lines, at values of 0.3 and 0.7, respectively, are visual guides only. The diagonal line indicates a slope of unity. Separation of cases and controls with cases moving to the right and controls moving to the left indicates improved risk assessments by inclusion of the 13 putative biomarkers.

Figure 5:
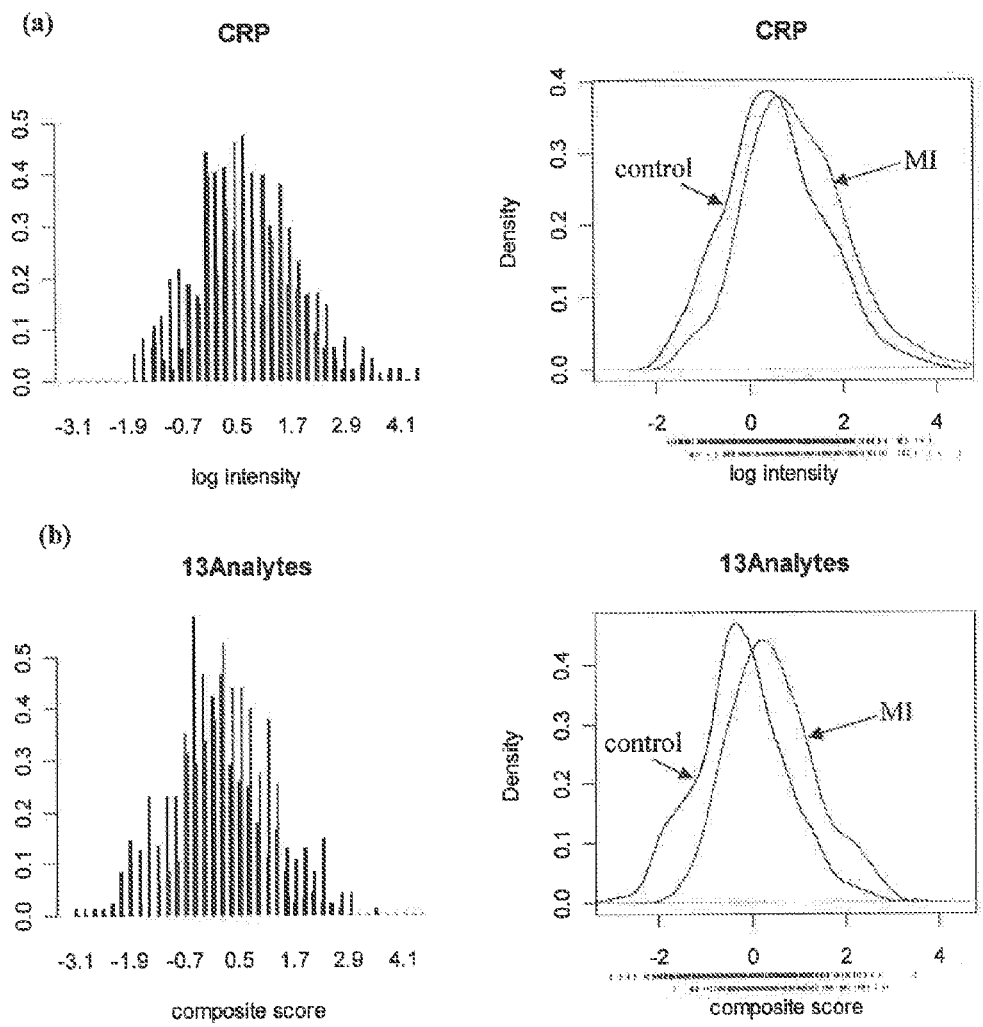
FIG. 5 shows baseline frequency distribution of 13 putative biomarker composite multimarker score, and analogous frequency distribution of C-reactive protein, among MI case subjects and control subjects, in accordance with an illustrative embodiment. Baseline frequency distributions are shown of (a) C-reactive protein; and (b) multimarker score comprising 13 biomarkers.

There was considerable overlap in the frequency distributions of individual established risk factors and biomarkers in those who developed a MI and those who did not. FIG. 5a shows the frequency distribution of C-reactive protein as an example. The multimarker score exhibited relatively less overlap in frequency distribution between events and non-events (FIG. 5b). More specifically, FIG. 5 shows baseline frequency distribution of 13 putative biomarker composite multimarker score, and analogous frequency distribution of C-reactive protein, among MI case subjects and control subjects, in accordance with an illustrative embodiment. Baseline frequency distributions of (a) C-reactive protein; and (b) multimarker score comprising 13 biomarkers (analytes) are shown. Left panels show histograms, and right panels show fitted distribution functions.

TABLE 5

Area Under Curve discrimination between near-term MI cases and controls.

| Established risk factors and putative biomarkers | AUC (95% CI) | Relative Integrated Discrimination Improvement (IDI)* | P for Relative IDI |
|---|---|---|---|
| Established risk factors† | 0.69 (0.65-0.73) | — | — |
| +Alpha-1 antitrypsin | 0.71 (0.67-0.75) | 1.6% | <0.001 |
| +Alpha-1 antitrypsin, Iron | 0.72 (0.67-0.76) | 2.1% | <0.001 |
| +Alpha-1 antitrypsin, Iron, CRP | 0.72 (0.68-0.76) | 2.3% | <0.001 |
| +Alpha-1 antitrypsin, Iron, CRP, Creatinine | 0.74 (0.70-0.77) | 2.9% | <0.001 |

TABLE 5-continued

Area Under Curve discrimination between near-term MI cases and controls.

| Established risk factors and putative biomarkers | AUC (95% CI) | Relative Integrated Discrimination Improvement (IDI)* | P for Relative IDI |
|---|---|---|---|
| +Alpha-1 antitrypsin, Iron, CRP, Creatinine, Fibrinogen | 0.74 (0.70-0.78) | 3.2% | <0.001 |
| +13 putative biomarkers‡ | 0.74 (0.70-0.78) | 4.3% | <0.001 |

AUC, area under the receiver operating characteristic curve;
CI, confidence interval;
CRP, C-reactive protein.
*Relative to model comprising only established risk factors.
†Established risk factors are total cholesterol, HDL cholesterol, triglycerides, hypertension, smoking status, diabetes, familial history of premature MI, body mass index, and physical activity.
‡ Putative biomarkers are alpha-1 antitrypsin, C-reactive protein, creatinine, fibrinogen, transferrin saturation, alkaline phosphatase, apolipoprotein A1, apolipoprotein B, apolipoprotein E, complement C3, gamma-glutamyl transpeptidase, lymphocyte count, and neutrophil count.

Discussion

The present study in apparently healthy men and women shows that some established risk factors for 10-year and lifetime risks of MI are also associated with near-term (four-year) risk of MI. In addition, five among seventeen putative biomarkers were found to be independently associated with near-term MI and improved risk model fit after adjustment for established risk factors. Most events occurred in people belonging to the low or intermediate Framingham risk categories, particularly among females.

Risk Factors

The most common cause of MI is rupture of an inflamed fibrous cap of a vulnerable plaque leading to coronary thrombosis. (Thim T, Hagensen M K, Bentzon J F, Falk E. From vulnerable plaque to atherothrombosis. *J. Intern. Med.* 263: 506-16 (2008)). It has been suggested that systemic markers of inflammation and/or a prothrombotic state would be particularly predictive for such local inflammation-related atherothrombotic events. (Koenig W, Khuseyinova N. Biomarkers of atherosclerotic plaque instability and rupture. *Arterioscler. Thromb. Vasc. Biol.* 27:15-26 (2007)). To assess this hypothesis, several inflammation-sensitive plasma proteins were included in the putative biomarker panel (CRP, fibrinogen, $\alpha_1$-antitrypsin, and complement component 3) of which some also might promote thrombosis. Three of these inflammation-related biomarkers were independently associated with increased risk of a near-term MI.

The association between CRP and near-term MI was virtual identical to that previously reported in both short term (Ridker P M, Cushman M, Stampfer M J, Tracy R P, Hennekens C H. Inflammation, aspirin, and the risk of cardiovascular disease in apparently healthy men. *N. Engl. J. Med.* 336: 973-9 (1997)) and longer-term studies (Ridker P M. C-reactive protein and the prediction of cardiovascular events among those at intermediate risk: moving an inflammatory hypothesis toward consensus. *J. Am. Coll. Cardiol.* 49:2129-38 (2007)), consistent with observations that indicate that CRP is neither a marker nor a mediator of atherothrombosis (Pepys MB. C-reactive protein is neither a marker nor a mediator of atherosclerosis. *Nat. Clin. Pract. Nephrol.* 4:234-5 (2008)). Previously, no association was found between local inflammation (macrophage density) in symptomatic carotid plaques removed by surgery and CRP levels in the blood (Grønholdt M L, Nordestgaard B G, Bentzon J, et al. Macrophages are associated with lipid-rich carotid artery plaques, echolucency on B-mode imaging, and elevated plasma lipid levels. *J. Vasc. Surg.* 35:137-45 (2002)), arguing against a direct link between inflammation in a single high-risk (vulnerable) or symptomatic plaque and circulating CRP. Furthermore, a large genetic epidemiological study based on the principle of Mendelian randomization provided no support for a causal role of CRP in atherothrombosis and MI. (Zacho J, Tybjaerg-Hansen A, Jensen J S, Grande P, Sillesen H, Nordestgaard B G. Genetically elevated C-reactive protein and ischemic vascular disease. *N. Engl. J. Med.* 359:1897-908 (2008)). Nevertheless, CRP could still be useful clinically in risk assessment and management of individuals at-risk of a MI. (Ridker P M, Danielson E, Fonseca F A, et al. Rosuvastatin to prevent vascular events in men and women with elevated C-reactive protein. *N. Engl. J. Med.* 359:2195-207 (2008)).

Among the other systemic inflammation-sensitive proteins assessed in the present study, fibrinogen deserves special attention because of its multifunctional role in inflammation, plasma viscosity, coagulation, and platelet aggregation. (Koenig W. Fibrin(ogen) in cardiovascular disease: an update. *Thromb. Haemost.* 89:601-9 (2003)). The strength of association between fibrinogen and near-term MI was similar to that previously reported in longer-term studies. However, a possible causal role of fibrinogen in atherothrombosis and MI has not been substantiated in genetic epidemiological studies (Mendelian randomization) and remains hypothetical. (Tybjaerg-Hansen A, Agerholm-Larsen B, Humphries S E, Abildgaard S, Schnohr P, Nordestgaard B G. A common mutation (G-455-->A) in the beta-fibrinogen promoter is an independent predictor of plasma fibrinogen, but not of ischemic heart disease. A study of 9,127 individuals based on the Copenhagen City Heart Study. *J Clin Invest.* 99:3034-9 (1997))

As previously reported in longer-term studies (Engström G, Lind P, Hedblad B, Stavenow L, Janzon L, Lindgärde F. Effects of cholesterol and inflammation-sensitive plasma proteins on incidence of MI and stroke in men. *Circulation* 105:2632-7 (2002)), α1-antitrypsin was also associated with near-term risk of MI with a strength comparable to that of CRP and fibrinogen. Indeed, these three inflammation-sensitive plasma proteins correlated positively with each other in the present study. $\alpha_1$-Antitrypsin is the main proteinase inhibitor in human plasma, synthesized primarily in the liver as well as by neutrophils and monocyte/macrophages. Its concentration has been reported to be relatively high in human atherosclerotic lesions. (Smith E B. Molecular interactions in human atherosclerotic plaques. *Am J. Pathol.* 86:665-74 (1977)) Genetic $\alpha_1$-antitrypsin deficiency is associated with reduced risk of MI but also with reduced blood pressure. (Dahl M, Tybjaerg-Hansen A, Sillesen H, Jensen G, Steffensen R, Nordestgaard B G. Blood pressure, risk of ischemic cerebrovascular and ischemic heart disease, and longevity in alpha(1)-antitrypsin deficiency: the Copenhagen City Heart Study. *Circulation* 107:747-52 (2003)) The latter is a confounding factor regarding a possible causal role of $\alpha_1$-antitrypsin in atherothrombosis and MI.

Markers of iron overload (high serum iron and transferrin saturation) were associated with reduced risk of a near-term MI. Results from longer-term epidemiological studies are conflicting but, overall, do not support the existence of a strong association between iron status and MI. (Danesh J, Appleby P. Coronary heart disease and iron status: meta-analyses of prospective studies. *Circulation* 99:852-4 (1999)) Iron overload caused by mutations in the hemochromatosis gene does not appear to influence the risk of MI substantially. (van der A D L, Rovers M M, Grobbee D E, et al. Mutations in the HFE Gene and Cardiovascular Disease Risk: An Individual Patient Data Meta-Analysis of 53 880 Subjects. Circ Cardiovasc Genet. 1;43-50 (2008)) Nevertheless, the observed associations between low serum iron and transferrin saturation and increased risk of a near-term MI in an apparently healthy population deserve to be explored further.

Chronic renal failure is associated with a markedly increased risk of CVD (Sarnak M J, Levey A S, Schoolwerth A C, et al. American Heart Association Councils on Kidney in Cardiovascular Disease, High Blood Pressure Research, Clinical Cardiology, and Epidemiology and Prevention. Kidney disease as a risk factor for development of cardiovascular disease: a statement from the American Heart Association Councils on Kidney in Cardiovascular Disease, High Blood Pressure Research, Clinical Cardiology, and Epidemiology and Prevention. *Circulation* 108:2154-69 (2003)), but conflicting results have been published on the association between creatinine and long-term risk of MI in the general population. In our study, those in the top quintile had a double risk of a near-time MI compared to the bottom quintile after adjustment for established risk factors, including blood pressure and use of antihypertensive medication. Furthermore, creatinine did not correlate with any of the inflammation-sensitive proteins (CRP, fibrinogens, $\alpha_1$-antitrypsin). Possible explanations for the increased risk of CVD seen with elevated serum creatinine levels have been discussed previously. Id.

Prediction of Risk

In the prevention of MI, the importance of modifiable risk factors cannot be overstated. They account for most of the risk of atherosclerotic CVD worldwide. (Yusuf S, Hawken S, Ounpuu S, et al. Effect of potentially modifiable risk factors associated with MI in 52 countries (the INTERHEART study): case-control study. *Lancet.* 364:937-52 (2004)) A major problem is, however, that except for age and sex, established risk factors are poor predictors of risk. Most people destined for a first heart attack or stroke are unaware of their risk because their established risk factor levels are not unusually high. (Lauer M S. Primary prevention of atherosclerotic cardiovascular disease: the high public burden of low individual risk. *JAMA.* 297:1376-8 (2007)) Conversely, many individuals with an apparently adverse risk factor profile remain asymptomatic.

In the present study, only 13% of all near-term MI in females occurred in those categorized as high risk at baseline by the Framingham Risk Score. In men, about 50% of near-term MI occurred in the high-risk category. Although such depressing figures are often not reported directly, they can be computed from published data and seem to reflect the reality. In the Framingham Heart Study (Wilson P W F, Pencina M, Jacques P, Selhub J, D'Agostino R, O'Donnell C J. C-reactive protein and reclassification of cardiovascular risk in the Framingham Heart Study. *Circ Cardiovasc Qual Outcomes.* 1:92-7 (2008)), the Physicians' Health Study (Ridker P M, Paynter N P, Rifai N, Gaziano J M, Cook N R. C-reactive protein and Parental History Improve Global Cardiovascular Risk Prediction. The Reynolds Risk Score for Men. *Circulation* 118:2243-51 (2008)), the Women' Health Study (Ridker P M, Buring J E, Rifai N, Cook N R. Development and validation of improved algorithms for the assessment of global cardiovascular risk in women: the Reynolds Risk Score. *JAMA.* 297(6):611-9 (2007)), and the Northwick Park Heart Study (Shah T, Casas J P, Cooper J A, et al. Critical appraisal of CRP measurement for the prediction of coronary heart disease events: new data and systematic review of 31 prospective cohorts. *Int J Epidemiol.* 38:217-31 (2009)) more than 75% of all hard coronary events occurred in people classified at low or intermediate risk. Risk assessment is particularly difficult and unreliable in women.

With the established risk-factor based approach in primary prevention, most individuals destined for a near-term heart attack or stroke are misclassified and not identified as being at high risk. (Lauer M S. Primary prevention of atherosclerotic cardiovascular disease: the high public burden of low individual risk. *JAMA*. 297:1376-8 (2007)) Consequently, they are not offered the best available preventive therapy. Atherosclerotic CVD has a long incubation period which offers unique opportunities for the detection and treatment of vascular disease in its preclinical (asymptomatic) phase. Vascular imaging has the potential to provide a comprehensive assessment of subclinical atherosclerosis, including detection of plaque burden, plaque vulnerability and disease activity. (Naghavi M, Falk E, Hecht H S, et al. From vulnerable plaque to vulnerable patient—Part III: Executive summary of the Screening for Heart Attack Prevention and Education (SHAPE) Task Force report. *Am J Cardiol*. 98:2 H-15H (2006)). Such efforts are ongoing, including the High Risk Plaque Initiative. (http://www.hrpinitiative.com. The High Risk Plaque Initiative (2009)) Detection of subclinical atherosclerosis by noninvasive imaging and/or several circulating biomarkers combined, as in the present study for prediction of near-term MI, may improve risk assessment in the primary prevention of atherosclerotic CVD and may thus in the near future enter clinical practice.

Conclusions

Each of the five biomarkers individually were associated with increased near-term (four years) risk of MI independent of established risk factors. Moreover, the set of 13 biomarkers combined provided a 9-fold increase in predictive risk of near-term MI. Thus, the risk factors for predicting near-term MI likely are quite different from those for predicting long-term CVD events, at least in this Copenhagen population.

EXAMPLE 2

The study population, established risk factors, and putative biomarkers are as described in Example 1. The variables representing established risk factors were treated as described in Example 1, and the variables representing the putative biomarkers were treated as continuous variables.

A logistic regression model was used to examine association between baseline variable levels and incidence of MI. This model included 13 biomarkers identified in Example 1 and listed in Table 6.

An exemplary equation for determining a risk score indicative of a person's risk of developing a MI is calculated by multiplying the measurement level of each biomarker by a coefficient reflecting its relative contribution to risk, and summing linearly each multiplication product to yield a risk score. The measurement levels of each biomarker are natural logarithmically transformed (i.e. using base e, where e is approximately 2.71828183) prior to multiplication with the coefficient. As one skilled in the art will recognize, a constant term can be added to this sum of multiplication products in order to calibrate the calculated risk probability to the observed risk.

For this example and model, the 13 biomarkers identified in Example 1 and Table 6 were used. A logistic regression model was used to determine the coefficients associated with each of the 13 markers.

TABLE 6

Biomarker coefficients for Example 2.

| biomarker | coefficient | coefficient identifier |
|---|---|---|
| neutrophil count | 0.281 | b1 |
| lymphocyte count | −0.196 | b2 |
| fibrinogen | −0.239 | b3 |
| creatinine | 1.396 | b4 |
| gamma-glutamyl transpeptidase | 0.117 | b5 |
| alkaline phosphatase | 0.857 | b6 |
| apolipoprotein B | 1.125 | b7 |
| apolipoprotein A1 | −1.484 | b8 |
| apolipoprotein E | 0.211 | b9 |
| alpha-1 antitrypsin | 1.589 | b10 |
| complement C3 | 0.374 | b11 |
| high-sensitivity CRP | 0.164 | b12 |
| transferrin saturation | −0.485 | b13 |

The units of measurement for each of the biochemical markers in Table 6 are as follows:

TABLE 7

Biomarker units for Example 2.

| biomarker | units |
|---|---|
| neutrophil count | $10^9$ cells/liter |
| lymphocyte count | $10^9$ cells/liter |
| fibrinogen | micromol |
| creatinine | micromol |
| gamma-glutamyl transpeptidase | units per liter |
| alkaline phosphatase | units per liter |
| apolipoprotein B | grams per liter |
| apolipoprotein A1 | grams per liter |
| apolipoprotein E | milligrams per liter |
| alpha-1 antitrypsin | micromol |
| complement C3 | grams per liter |
| high-sensitivity CRP | milligrams per liter |
| transferrin saturation | percent |

Accordingly, a risk score for an individual using this model can be determined as follows:

$$b_1*\ln(\text{neutrophil count}) + b_2*\ln(\text{lymphocyte count}) + b_3*\ln(\text{fibrinogen}) + b_4*\ln(\text{creatinine}) + b_5*\ln(\text{gamma-glutamyl transpeptidase}) + b_6*\ln(\text{alkaline phosphatase}) + b_7*\ln(\text{apolipoprotein B}) + b_8*\ln(\text{apolipoprotein A1}) + b_9*\ln(\text{apolipoprotein E}) + b_{10}*\ln(\text{alpha-1 antitrypsin}) + b_{11}*\ln(\text{complement C3}) + b_{12}*\ln(\text{high-sensitivity C-reactive protein}) + b_{12}*\ln(\text{transferrin saturation})$$

where b1 through b13 are the coefficients listed in Table 6, and ln(x) indicates the logarithmically transformed value of x using base e.

Figure 6:
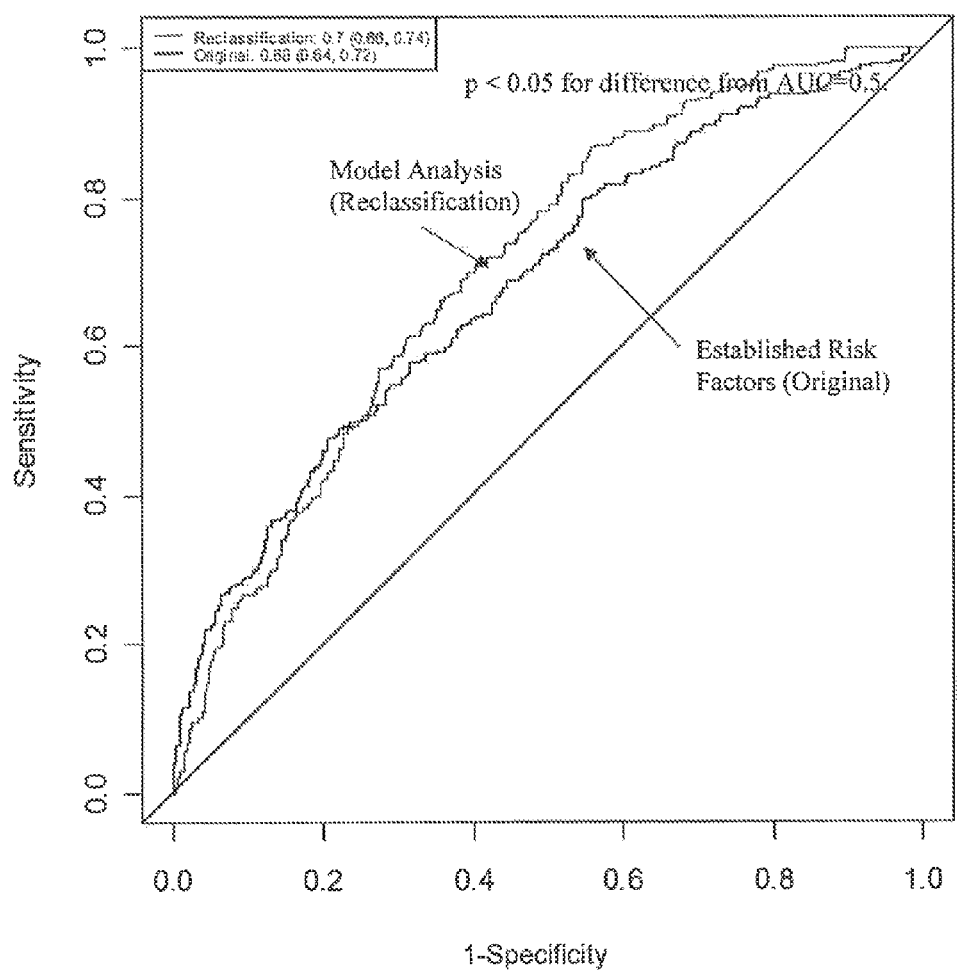
FIG. 6 is a receiver-operating characteristic curve demonstrating the performance of a model risk analysis for predicting a future MI in 751 subjects, in accordance with an illustrative embodiment.

FIG. 6 is a ROC curve demonstrating the performance of this analysis in predicting a future MI in these 751 subjects. As can be seen in FIG. 6, this analysis using the 13 biomarkers listed in Table 6 is a statistically significant predictor of the risk of near-term MI, with a p-value <0.05 when compared to the futilty line in the ROC curve.

EXAMPLE 3

The study population, established risk factors, and putative biomarkers are as described in Example 1. The variables representing established risk factors were treated as described in Example 1, and the variables representing the putative biomarkers were treated as continuous variables.

A logistic regression model was used to examine association between baseline variable levels and incidence of MI.

This example initially considered the 13 biomarkers identified in Example 1 (the same starting set used in Example 2 above).

A backward stepwise variable selection technique was used in order to select an informative subset of biomarkers from among these initial thirteen biomarkers. At each stepwise selection step, a biomarker was retained if the p-value associated with its coefficient was p<0.05. In this manner, seven biomarkers were retained for the final model. Table 8 lists their coefficients:

TABLE 8

Biomarker coefficients for Example 3.

| biochemical marker | coefficient | coefficient identifier |
|---|---|---|
| creatinine | 1.320 | b1 |
| alkaline phosphatase | 0.959 | b2 |
| apolipoprotein B | 1.287 | b3 |
| apolipoprotein A1 | −1.224 | b4 |
| alpha-1 antitrypsin | 1.626 | b5 |
| high-sensitivity CRP | 0.202 | b6 |
| transferrin saturation | −0.476 | b7 |

The measurement units for these biomarkers are as noted in Table 7 in Example 2.

Accordingly, a risk score for an individual using this model can be determined as follows:

b1*ln(creatinine)+b2*ln(alkaline phosphatase)+b3*ln
 (apolipoprotein B)+b4*ln(apolipoprotein A1)+
 b5*ln(alpha-1 antitrypsin)+b6*ln(high-sensitivity
 C-reactive protein)+b7*ln(transferrin saturation)

where b1 through b7 are the coefficients listed in Table 8, and ln(x) indicates the logarithmically transformed value of x using base e.

Figure 7:
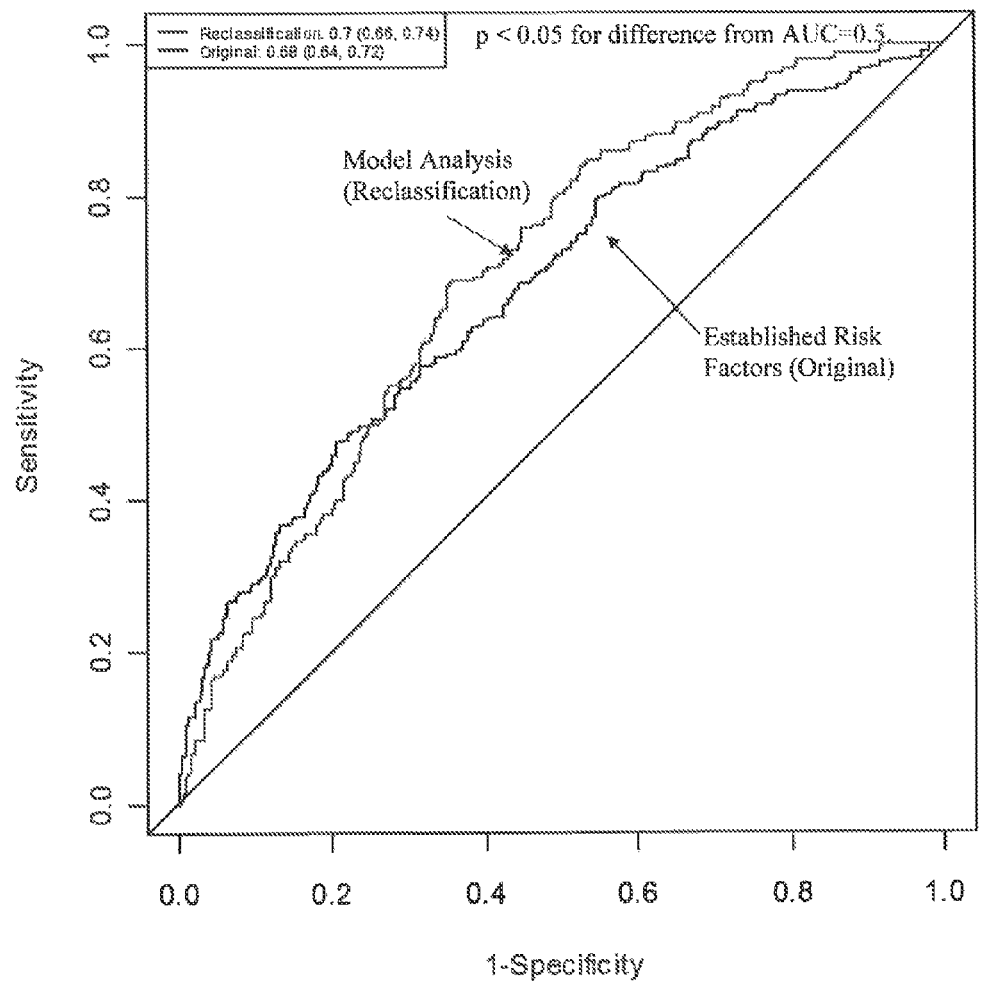
FIG. 7 is a receiver-operating characteristic curve demonstrating the performance of a model risk analysis for predicting a future MI in 751 subjects, in accordance with an illustrative embodiment.

FIG. 7 is a ROC curve demonstrating the performance of this analysis in predicting a future MI in these 751 subjects. As can be seen in FIG. 7, this analysis using the seven biomarkers listed in Table 8 is a statistically significant predictor of the risk of near-term MI, with a p-value <0.05 when compared to the futilty line in the ROC curve.

EXAMPLE 4

The study population, established risk factors, and putative biomarkers are as described in Example 1. The variables representing established risk factors were treated as described in Example 1, and the variables representing the putative biomarkers were treated as continuous variables.

This example considered the seven biomarkers identified in Example 3, in conjunction with the following nine established clinical risk factors: smoking status, diabetes status, hypertension, total cholesterol level, HDL cholesterol level, body mass index, physical inactivity status, familial history of premature MI, and triglyceride level.

The nine established clinical risk factors were determined and/or defined as described above in Example 1.

The nine established clinical risk factor variables were treated statistically as follows. Total cholesterol was divided into five levels (less than 4.8 mM, 4.8-5.4 mM, 5.4-6.0 mM, 6.0-6.6 mM, greater than 6.6 mM), HDL cholesterol was divided into five levels (less than 1.14 mM, 1.14-1.40 mM, 1.40-1.65 mM, 1.65-2.00 mM, greater than 2.00 mM), triglyceride level was treated as a continuous variable (with measurement units of mM), five blood pressure categories (systolic/diastolic pressure <120/80 mmHg, ≥120/80 and <130/85 mmHg, ≥130/85 and <140/90 mmHg, ≥140/90 and <160/100 mmHg, or ≥160/100 mmHg or use of antihypertensive therapy), smoking status (never smoked, current smoker, former smoker), diabetes mellitus (yes/no), family history of premature MI (yes/no), body mass index (treated as a continuous variable) and physical activity (dichotomized, less than four hours of activity per week and sedentary work, or greater than 4 hours of activity per week and/or non-sedentary work).

A logistic regression model was used to examine association between baseline variable levels and incidence of MI. This model included seven biomarkers and the nine established clinical factors.

A logistic regression model was used to determine the coefficients associated with each of the variables.

TABLE 9

Traditional risk factor coefficients for Example 4.

| variable | coefficient |
|---|---|
| smoker: never | 0 |
| smoker: former | 0.1848 |
| smoker: current | 0.8016 |
| diabetes: yes | 0.5542 |
| diabetes: no | 0 |
| hypertension: <120/80 mmHg | 0 |
| hypertension: ≥120/80& <130/85 mmHg | −0.1279 |
| hypertension: ≥130/85& <140/90 mmHg | 0.5371 |
| hypertension: ≥140/90& <160/100 mmHg | 0.1659 |
| hypertension: ≥160/100 mmHg or use of antihypertensive therapy | 0.8854 |
| total cholesterol <4.8 mM | 0 |
| total cholesterol 4.8-5.4 mM | −0.2074 |
| total cholesterol 5.4-6.0 mM | −0.2383 |
| total cholesterol 6.0-6.6 mM | −0.0215 |
| total cholesterol >6.6 mM | 0.435 |
| HDL cholesterol <1.14 mM | 0 |
| HDL cholesterol 1.14-1.40 mM | −0.246 |
| HDL cholesterol 1.40-1.65 mM | −0.067 |
| HDL cholesterol 1.65-2.00 mM | −0.1351 |
| HDL cholesterol >2.00 mM | −0.2844 |
| Body mass index | 0.0163 |
| physical activity:, less than 4 hours of activity per week and sedentary work | −0.0411 |
| physical activity: greater than 4 hours of activity per week and/or non-sedentary work | 0 |
| family history of premature MI: no | 0 |
| family history of premature MI: yes | 0.7587 |
| triglyceride level | 0.0709 |
| creatinine | 1.3182 |
| alkaline phosphatase | 0.8232 |
| apolipoprotein B | 0.6724 |
| apolipoprotein A1 | −1.2771 |
| alpha-1 antitrypsin | 1.4605 |
| high-sensitivity C-reactive protein | 0.1609 |
| transferrin saturation | −0.4859 |

A risk score for an individual using this model was calculated by multiplying the measurement level or value of each variable by a coefficient reflecting its relative contribution to risk, and summing linearly each multiplication product to yield a risk probability. The measurement levels of variables treated as continuous variables in the table above (i.e. body mass index, triglyceride level, creatinine, alkaline phosphatase, apolipoprotein B, apolipoprotein A1, alpha-1 antitrypsin, high-sensitivity C-reactive protein, and transferrin saturation) are natural logarithmically transformed (i.e. using base e, where e is approximately 2.71828183) prior to multiplication with the coefficient. For categorical variables, the coefficient associated with an individual's category is multiplied by unity (for example, an HDL cholesterol of 1.5 mM would contribute −0.067*1 to the final risk score). As one skilled in the art will recognize, a constant term can be added to this sum of multiplication products in order to calibrate the calculated risk probability to the observed risk.

Figure 8:
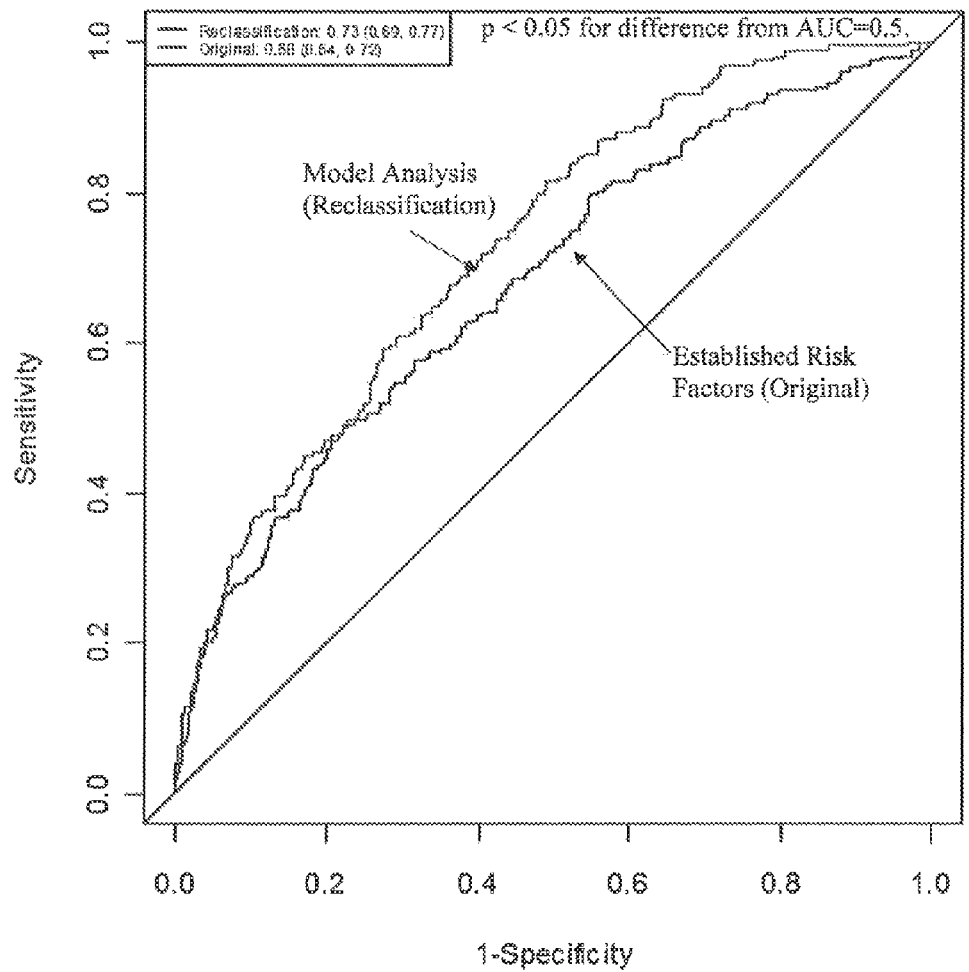
FIG. 8 is a receiver-operating characteristic curve demonstrating the performance of a model risk analysis for predicting a future MI in 751 subjects, in accordance with an illustrative embodiment.

FIG. 8 is a ROC curve demonstrating the performance of this analysis in predicting a future MI in these 751 subjects. As can be seen in FIG. 8, this analysis using the seven biomarkers listed in Table 8 along with the traditional risk factors (in totality, listed in Table 9) is a statistically significant predictor of the risk of near-term MI, with a p-value <0.05 when compared to the futilty line in the ROC curve.

EXAMPLE 5

The study population, established risk factors, and putative biomarkers are as described in Example 1. The variables representing established risk factors and putative biomarkers were treated as continuous variables, except for blood pressure (which was categorized into five categories (systolic/diastolic pressure less than 120/80 mmHg, ≥120/80 and <130/85 mmHg, ≥130/85 and <140/90 mmHg, ≥140/90 and <160/100 mmHg, or ≥160/100 mmHg or use of antihypertensive therapy), smoking status (never smoked, current smoker, former smoker), diabetes mellitus (yes/no), family history of premature MI (yes/no), body mass index (treated as a continuous variable) and physical activity (dichotomized, less than four hours of activity per week and sedentary work, or greater than four hours of activity per week and/or non-sedentary work).

A logistic regression model was used to examine association between baseline variable levels and incidence of MI. This model included eight biomarkers identified in Example 1 and listed in Table 10 below.

A logistic regression model was used to determine the coefficients associated with each of the 8 biomarkers.

TABLE 10

Biomarker coefficients for Example 5.

| biomarker | coefficient | coefficient identifier |
|---|---|---|
| apolipoprotein B | 0.00928 | b1 |
| apolipoprotein A1 | −0.00991 | b2 |
| transferrin | 0.03099 | b3 |
| alpha-1 antitrypsin | 0.07438 | b4 |
| alpha fetoprotein | −0.5687 | b5 |
| beta-2-microglobulin | 1.49583 | b6 |
| carcinoembryonic antigen | 0.60629 | b7 |
| vascular endothelial growth factor | 0.6066 | b8 |

The units of measurement for each of the biomarkers in Table 10 are as follows:

TABLE 11

Biomarker units for Example 5.

| biomarker | units |
|---|---|
| apolipoprotein B | grams per liter |
| apolipoprotein A1 | grams per liter |
| transferrin | micromol |
| alpha-1 antitrypsin | micromol |
| alpha fetoprotein | nanogram per milliliter |
| beta-2-microglobulin | microgram per milliliter |
| carcinoembryonic antigen | nanogram per milliliter |
| vascular endothelial growth factor | picogram per milliliter |

Accordingly, a risk score for an individual using this model can be determined as follows:

b1*ln(apolipoprotein B)+b2*ln(apolipoprotein A1)+
b3*ln(transferrin)+b4*ln(alpha-1 antitrypsin)+
b5*ln(alpha fetoprotein)+b6*ln(beta-2-microglobulin)+b7*ln(carcinoembryonic antigen)+b8*ln(vascular endothelial growth factor)

where b1 through b8 are the coefficients listed in Table 10, and ln(x) indicates the logarithmically transformed value of x using base e.

The performance of this model was evaluated as follows. The score from this model was calculated for each individual. As well, a score derived from a logistic regression analysis considering solely the nine established clinical risk factors (smoking status, diabetes status, hypertension, total cholesterol level, HDL cholesterol level, body mass index, physical inactivity status, familial history of premature MI, and triglyceride level) was also computed. (See Examples 1 and 3 for details on the categorization and definition of these 9 established clinical risk factors.) Subsequently, the area under the ROC curve ('AUC') was calculated for the model comprising the eight biomarkers based on the score, and for the model comprising solely the nine established clinical risk factors. In addition, the net reclassification improvement ('NRI'), integrated discrimination improvement ('IDI'), and relative integrated discrimination improvement ('relative IDI') were calculated for the model comprising the eight biomarkers based on the score, relative to the model comprising solely the nine established clinical risk factors. The results are as follows:

AUC for 8 biomarker model: 0.73 (95% confidence interval (CI): 0.69-0.77)

AUC for 9 established risk factor model: 0.68 (95% CI: 0.63-0.72)

p-value for difference in AUC between two models: p=0.027

NRI=15.1% (p<0.01)

IDI=6.8% (p<0.01)

relative IDI=4.7% (p<0.01).

(NRI, IDI, and relative IDI, and the respective p values, are calculated as discussed in: Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2): 157-72.)

Thus, this analysis using the eight biomarkers listed in Table 10 is a better predictor of the risk of near-term MI than the traditional risk factors.

EXAMPLE 6

The study population, established risk factors, and putative biomarkers are as described in Example 1. The variables representing established risk factors and putative biomarkers were treated as continuous variables, except for blood pressure (which was categorized into five categories (systolic/diastolic pressure less than 120/80 mmHg, ≥120/80 and <130/85 mmHg, ≥130/85 and <140/90 mmHg, ≥140/90 and <160/100 mmHg, or ≥160/100 mmHg or use of antihypertensive therapy), smoking status (never smoked, current smoker, former smoker), diabetes mellitus (yes/no), family history of premature MI (yes/no), body mass index (treated as a continuous variable) and physical activity (dichotomized, less than four hours of activity per week and sedentary work, or greater than four hours of activity per week and/or non-sedentary work).

A logistic regression model was used to examine association between baseline variable levels and incidence of MI. The model in this example comprises seven of the eight biomarkers that were used in the model of Example 5, namely: apolipoprotein B, apolipoprotein A1, transferrin, alpha-1 antitrypsin, alpha-fetoprotein, beta-2-microglobulin, and carcinoembryonic antigen. It was found that the exclusion of vascular endothelial growth factor from the model did not degrade its performance in predicting risk of MI.

TABLE 12

Biomarker coefficients for Example 6.

| biomarker | coefficient | coefficient identifier |
|---|---|---|
| apolipoprotein B | 0.009425413 | b1 |
| apolipoprotein A1 | −0.009877646 | b2 |
| transferrin | 0.033005052 | b3 |
| alpha-1 antitrypsin | 0.077476562 | b4 |
| alpha fetoprotein | −0.541848132 | b5 |
| beta-2-microglobulin | 1.744238787 | b6 |
| carcinoembryonic antigen | 0.632458131 | b7 |

The units of measurements of each of the biomarkers are as follows:

TABLE 13

Biomarker units for Example 6.

| biomarker | units |
|---|---|
| apolipoprotein B | grams per liter |
| apolipoprotein A1 | grams per liter |
| transferrin | micromol |
| alpha-1 antitrypsin | micromol |
| alpha fetoprotein | nanogram per milliliter |
| beta-2-microglobulin | microgram per milliliter |
| carcinoembryonic antigen | nanogram per milliliter |

Accordingly, a risk score for an individual using this model can be determined as follows:

b1*ln(apolipoprotein B)+b2*ln(apolipoprotein A1)+ b3*ln(transferrin)+b4*ln(alpha-1 antitrypsin)+ b5*ln(alpha fetoprotein)+b6*ln(beta-2-microglo- bulin)+b7*ln(carcinoembryonic antigen)

where b1 through b7 are the coefficients listed in table 12, and ln(x) indicates the logarithmically transformed value of x using base e.

The score from this model was calculated for each individual. As well, a score derived from a logistic regression analysis considering solely the nine established clinical risk factors (smoking status, diabetes status, hypertension, total cholesterol level, HDL cholesterol level, body mass index, physical inactivity status, familial history of premature MI, and triglyceride level) was also computed. (See Examples 1 and 3 for details on the categorization and definition of these nine established clinical risk factors.) Subsequently, the area under the ROC curve ('AUC') was calculated for the model comprising the seven biomarkers based on the score, and for the model comprising solely the nine established clinical risk factors. In addition, the net reclassification improvement ('NRI'), integrated discrimination improvement ('IDI'), and relative integrated discrimination improvement ('relative IDI') were calculated for the model comprising the seven biomarkers based on the score, relative to the model comprising solely the nine established clinical risk factors. The results are as follows:

AUC for 7 biomarker model: 0.74 (95% confidence interval (CI): 0.71-0.78)

AUC for 9 established risk factor model: 0.68 (95% CI: 0.63-0.72)

p-value for difference in AUC between two models: p=0.007

NRI=20.9% (p<0.01)

IDI=8.2% (p<0.01)

relative IDI=5.6% (p<0.01).

NRI, IDI, and relative IDI, and the respective p values, are calculated as in Example 5

Thus, this analysis using the seven biomarkers listed in Table 12 is a better predictor of the risk of near term MI than the traditional risk factors.

EXAMPLE 7

The study population, established risk factors, and putative biomarkers are as described in Example 1. The variables representing putative biomarkers were treated as continuous variables.

Logistic regression models were evaluated to assess the association between baseline variables and incidence of MI. The model in this example comprises the following four blood plasma analytes, i.e., four biomarkers: alpha-1 antitrypsin, carcinoembryonic antigen, beta-2-microglobulin, and N-terminal B-type natriuretic peptide (NT-proBNP).

Model 1

An unconditional logistic regression model was fitted that included as predictor variables only the four blood plasma analytes, i.e., four biomarkers: alpha-1 antitrypsin, carcinoembryonic antigen, beta-2-microglobulin, and N-terminal B-type natriuretic peptide. Using statistical software (R software, version 2.6), the coefficients of each of the four analytes were estimated to be the following:

TABLE 14

Biomarker coefficients for Example 7, Model 1.

| biomarker | coefficient | coefficient identifier |
|---|---|---|
| alpha-1 antitrypsin | 1.116 | b1 |
| carcinoembryonic antigen | 0.433 | b2 |
| beta-2-microglobulin | 1.082 | b3 |
| NT-proBNP | 0.047 | b4 |

The units of measurements of each of the biomarkers are as follows:

TABLE 15

Biomarker units for Example 7, Model 1.

| biomarker | units |
|---|---|
| alpha-1 antitrypsin | micromol |
| carcinoembryonic antigen | nanogram per milliliter |
| beta-2-microglobulin | microgram per milliliter |
| NT-proBNP | picogram per milliliter |

Figure 9:
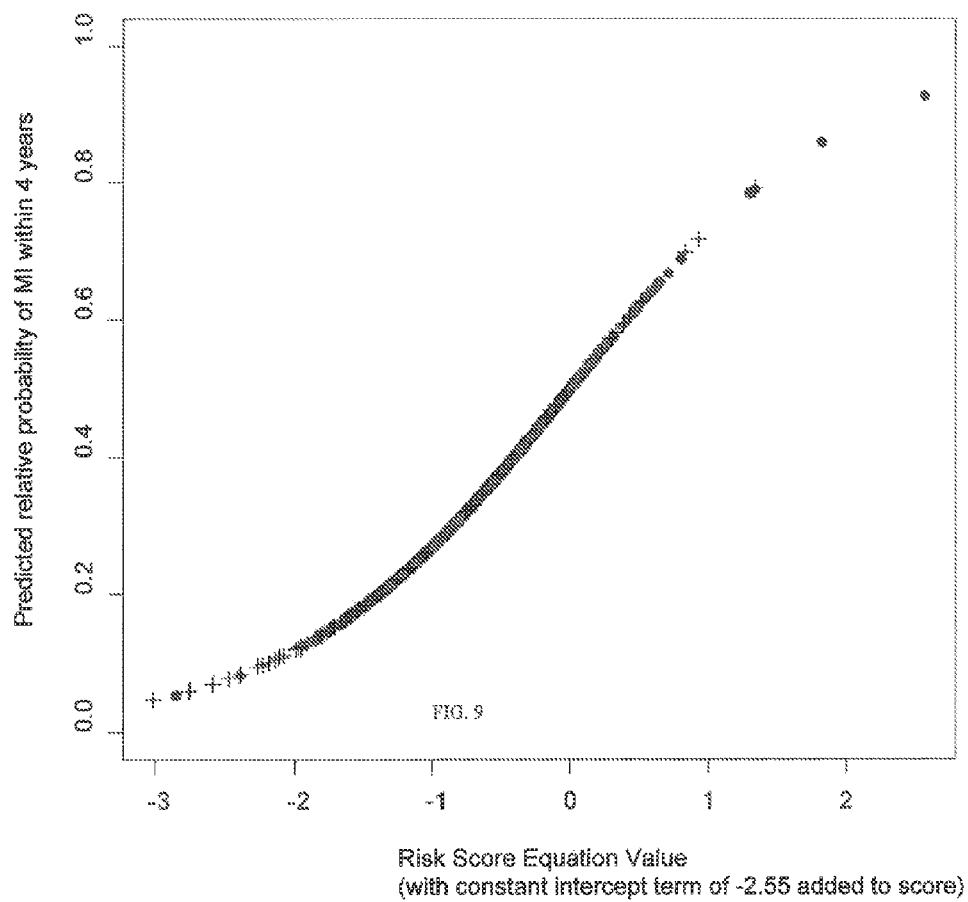
FIG. 9 is a curve of the relationship between a risk score derived in accordance with the present teachings and the relative probability of experiencing a MI within 4 years, in accordance with an illustrative embodiment.

Accordingly, a risk score for an individual using this model can be determined as follows:

b1*ln(alpha-1 antitrypsin)+b2*ln(carcinoembryonic antigen)+b3*ln(beta-2-microglobulin)+b4*ln (NT-proBNP)

where b1 through b4 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner, so long as the added constant term is added in the same manner to the risk score of every individual. A higher risk score represents an increased likelihood of MI within 4 years of testing. FIG. 9 illustrates the relationship between the risk score, derived from the equation above, and relative probability of MI within 4 years. In FIG. 9, crosses denote individuals who did not experience an MI within 4 years, and circles denote individuals who did experience an MI within 4 years. Note that a constant intercept value of negative 2.55 has been added to the risk score for every individual. Data are taken from a study of 751 individuals, 252 of whom experienced an MI within 4 years of blood testing. One possible threshold value from FIG. 9 would be that a risk score of value greater than or equal to 1 defines a high risk group, whereas a risk score value that is less than or equal to −1 defines a low risk group, with risk scores between −1 and 1 representing an intermediate risk group. One skilled in the art will recognize that such thresholds may differ based on a variety of clinically relevant factors, such as desired sensitivity, specificity, positive and negative predictive values, different age, gender, or ethnic or racial groups, and the like.

Figure 10A:
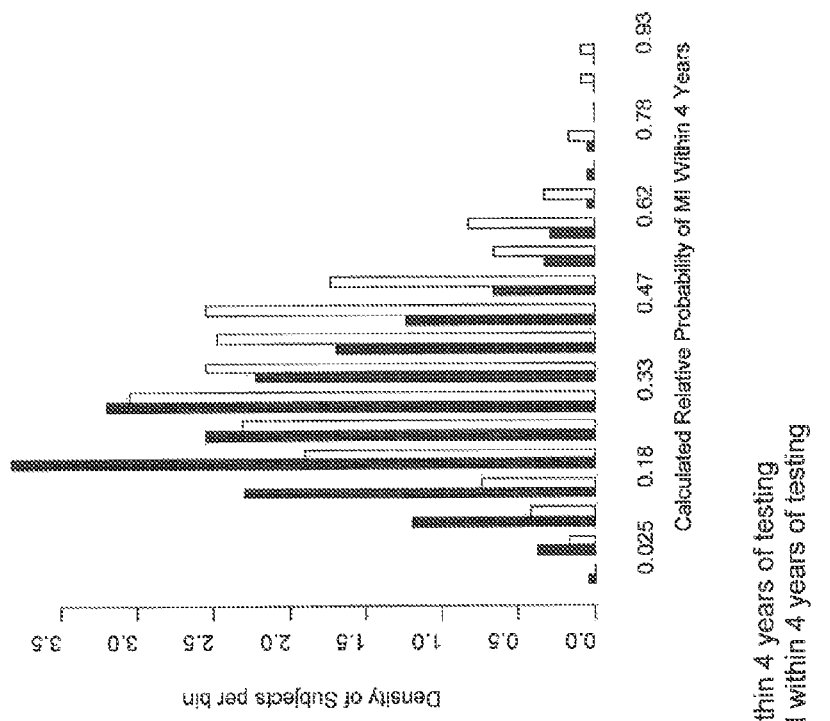
FIG. 10A is a graph of the distribution of risk scores among cases and controls, taken from a study of 751 individuals, 252 of whom experienced an MI within 4 years of blood testing, in accordance with an illustrative embodiment.
Figure 10B:
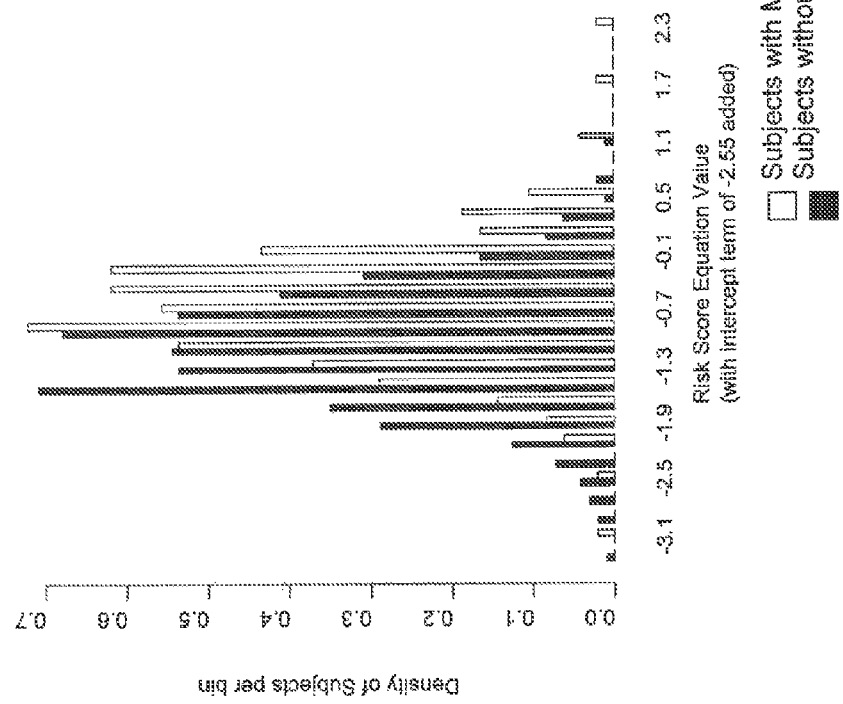
FIG. 10B is a graph of the distribution of predicted relative probability of a MI within 4 years, based on each subject's risk score value, for the subjects in a study of 751 individuals, 252 of whom experienced a MI within 4 years of blood testing, in accordance with an illustrative embodiment.

FIG. 10A illustrates the distribution risk scores among cases and controls, and FIG. 10B illustrates the distribution of predicted relative probability of MI within 4 years, based on each subject's risk score value, for the subjects in the study.

One skilled in the art will recognize that the coefficients associated with each analyte may differ depending on a variety of factors, such as measurement technology, laboratory environmental conditions, and blood specimen collection, storage and processing procedures, and measurement units, for example. The above coefficients associated with each analyte represent one particular embodiment.

FIG. 10A is a graphical representation of the distribution of the risk scores, calculated according to the equation above, for individuals who experienced a near-term MI and for individuals who did not experience a near-term MI in the study. FIG. 10B illustrates the distribution of predicted relative probability of MI within 4 years, based on each subject's risk score value.

The area under the receiver-operating characteristic (ROC) curve, "AUC," was calculated based on the risk score equation above derived from the four biomarkers. The AUC, and its accompanying 95% confidence interval (CI), was found to be 0.674 (95% CI: 0.631-0.715). This was found to be significantly different than the futility AUC value of 0.5 (at a significance level of $p<0.05$), which would indicate no predictive or prognostic accuracy. As such, it is concluded that the risk score based on the four biomarkers listed in Table 14 is a significant predictor of the risk of near term MI.

Model 2

An unconditional logistic regression model was fitted that included as predictor variables the four blood plasma analytes, i.e., four biomarkers: alpha-1 antitrypsin, carcinoembryonic antigen, beta-2-microglobulin, and N-terminal B-type natriuretic peptide, plus age. Using statistical software (R software, version 2.6), the coefficients of each of the five variables were estimated to be the following:

TABLE 16

Biomarker coefficients for Example 7, Model 2.

| biomarker | coefficient | coefficient identifier |
|---|---|---|
| alpha-1 antitrypsin | 1.161 | b1 |
| carcinoembryonic antigen | 0.487 | b2 |
| beta-2-microglobulin | 1.720 | b3 |
| NT-proBNP | 0.147 | b4 |
| age | −0.044 | b5 |

The units of measurements of each of the biomarkers are as follows:

TABLE 17

Biomarker units for Example 7, Model 2.

| biomarker | units |
|---|---|
| alpha-1 antitrypsin | micromol |
| carcinoembryonic antigen | nanogram per milliliter |
| beta-2-microglobulin | microgram per milliliter |
| NT-proBNP | picogram per milliliter |
| age | years |

Accordingly, a risk score for an individual using this model can be determined as follows:

b1*ln(alpha-1 antitrypsin)+b2*ln(carcinoembryonic antigen)+b3*ln(beta-2-microglobulin)+b4*ln(NT-proBNP)+b5*(age)

where b1 through b5 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The receiver-operating characteristic ('ROC') curve, 'AUC', was calculated based on the risk score equation above derived from the four biomarkers. The AUC, and its accompanying 95% confidence interval (CI), was found to be 0.704 (95% CI: 0.661-0.745). This was found to be significantly different than the futility AUC value of 0.5 ($p<0.05$). As such, it is concluded that the risk score based on the five biomarkers listed in Table 16 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the four blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising thirteen variables, was then compared to a model comprising only the nine variables representing traditional risk factors, and evidence for an improvement in risk prediction upon the addition of the four blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into five categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the four biomarkers based on the score plus the nine traditional risk factor variables, and for a model comprising solely the nine established clinical risk factors listed above (without the four biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2):157-72.) The results are as follows:

AUC for 4 biomarker model plus 9 traditional risk factors: 0.754 (95% confidence interval (CI): 0.714-0.790)
AUC for 9 established risk factors only: 0.682 (95% CI: 0.639-0.722)
p-value for difference in AUC between two models: p<0.001
IDI=7.9% (95% CI: 5.7%-10.0%), p<0.001

Thus, the addition of the 4 biomarkers, namely, alpha-1 antitrypsin, carcinoembryonic antigen, beta-2-microglobulin, and N-terminal B-type natriuretic peptide, to traditional risk factors yields a better set of biomarkers for risk prediction of near term MI than traditional risk factors alone.

EXAMPLE 8

The study population, established risk factors, and putative biomarkers are as described in Example 1. The variables representing putative biomarkers are treated as continuous variables.

Logistic regression models were evaluated to assess the association between baseline variables and incidence of MI. The model in this example comprises the following three blood plasma analytes, i.e., three biomarkers: alpha-1 antitrypsin, carcinoembryonic antigen, and beta-2-microglobulin.

Model 1

An unconditional logistic regression model was fitted that included as predictor variables only the three blood plasma analytes, i.e., three biomarkers: alpha-1 antitrypsin, carcinoembryonic antigen, and beta-2-microglobulin. Using statistical software (R software, version 2.6), the coefficients of each of the three analytes were estimated to be the following:

TABLE 18

Biomarker coefficients for Example 8, Model 1.

| biomarker | coefficient | coefficient identifier |
|---|---|---|
| alpha-1 antitrypsin | 1.167 | b1 |
| carcinoembryonic antigen | 0.438 | b2 |
| beta-2-microglobulin | 1.169 | b3 |

The units of measurements of each of the biomarkers are as follows:

TABLE 19

Biomarker units for Example 8, Model 1.

| biomarker | units |
|---|---|
| alpha-1 antitrypsin | micromol |
| carcinoembryonic antigen | nanogram per milliliter |
| beta-2-microglobulin | microgram per milliliter |

Accordingly, a risk score for an individual using this model can be determined as follows:

$$b1*\ln(\text{alpha-1 antitrypsin})+b2*\ln(\text{carcinoembryonic antigen})+b3*\ln(\text{beta-2-microglobulin})$$

where b1 through b3 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.67 (95% CI: 0.63-0.71). This was found to be significantly different than the futility AUC value of 0.5 (p<0.05). As such, it is concluded that the risk score based on the three biomarkers listed in Table 18 is a significant predictor of the risk of near term MI.

Model 2

An unconditional logistic regression model was fitted that included as predictor variables the three blood plasma analytes, i.e., three biomarkers: alpha-1 antitrypsin, carcinoembryonic antigen, beta-2-microglobulin, plus age. Using statistical software (R software, version 2.6), the coefficients of each of the five variables were estimated to be the following:

TABLE 20

Biomarker coefficients for Example 8, Model 2.

| biomarker | coefficient | coefficient identifier |
|---|---|---|
| alpha-1 antitrypsin | 1.297 | b1 |
| carcinoembryonic antigen | 0.491 | b2 |
| beta-2-microglobulin | 1.844 | b3 |
| age | −0.036 | b4 |

The units of measurements of each of the biomarkers are as follows:

TABLE 21

Biomarker units for Example 8, Model 2.

| biomarker | units |
|---|---|
| alpha-1 antitrypsin | micromol |
| carcinoembryonic antigen | nanogram per milliliter |
| beta-2-microglobulin | microgram per milliliter |
| age | years |

Accordingly, a risk score for an individual using this model can be determined as follows:

b1*ln(alpha-1 antitrypsin)+b2*ln(carcinoembryonic antigen)+b3*ln(beta-2-microglobulin)+b4*(age)

where b1 through b4 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.70 (95% CI: 0.65-0.74). This was found to be significantly different than the futility AUC value of 0.5 (p<0.05). As such, it is concluded that the risk score based on the four biomarkers listed in Table 20 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the three blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising twelve variables, was then compared to a model comprising only the nine variables representing traditional risk factors, and evidence for an improvement in risk prediction upon the addition of the three blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into five categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the three biomarkers based on the score plus the nine traditional risk factor variables, and for a model comprising solely the nine established clinical risk factors listed above (without the three biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2):157-72.) The results are as follows:

AUC for three biomarker model plus 9 traditional risk factors: 0.75 (95% confidence interval (CI): 0.71-0.78)

AUC for 9 established risk factors only: 0.68 (95% CI: 0.64-0.72)

p-value for difference in AUC between two models: p<0.001

IDI=6.6% (95% CI: 4.6%-8.6%), p<0.001

Thus, the addition of the three biomarkers, namely, alpha-1 antitrypsin, carcinoembryonic antigen, and beta-2-microglobulin, to traditional risk factors yields a better set of biomarkers for risk prediction of near term MI than traditional risk factors alone.

EXAMPLE 9

The study population, established risk factors, and putative biomarkers are as described in Example 1. The variables representing putative biomarkers are treated as continuous variables.

Logistic regression models were evaluated to assess the association between baseline variables and incidence of MI. The model in this example comprises the following three blood plasma analytes, i.e., three biomarkers: C-reactive protein, carcinoembryonic antigen, and beta-2-microglobulin.

Model 1

An unconditional logistic regression model was fitted that included as predictor variables only the three blood plasma analytes, i.e., three biomarkers: C-reactive protein, carcinoembryonic antigen, and beta-2-microglobulin. Using statistical software (R software, version 2.6), the coefficients of each of the three analytes were estimated to be the following:

TABLE 22

Biomarker coefficients for Example 9, Model 1.

| biomarker | coefficient | coefficient identifier |
|---|---|---|
| C-reactive protein | 0.027 | b1 |
| carcinoembryonic antigen | 0.448 | b2 |
| beta-2-microglobulin | 1.233 | b3 |

The units of measurements of each of the biomarkers are as follows:

TABLE 23

Biomarker units for Example 9, Model 1.

| biomarker | units |
|---|---|
| C-reactive protein | milligrams per liter |
| carcinoembryonic antigen | nanogram per milliliter |
| beta-2-microglobulin | microgram per milliliter |

Accordingly, a risk score for an individual using this model can be determined as follows:

b1*ln(C-reactive protein)+b2*ln(carcinoembryonic antigen)+b3*ln(beta-2-microglobulin)

where b1 through b3 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.66 (95% CI: 0.62-0.70). This was found to be significantly different than the futility AUC value of 0.5 (p<0.05). As such, it is concluded that the risk score based on the three biomarkers listed in Table 22 is a significant predictor of the risk of near term MI.

Model 2

An unconditional logistic regression model was fitted that included as predictor variables the three blood plasma analytes, i.e., three biomarkers: C-reactive protein, carcinoembryonic antigen and beta-2-microglobulin, plus age. Using statistical software (R software, version 2.6), the coefficients of each of the five variables were estimated to be the following:

TABLE 24

Biomarker coefficients for Example 9, Model 2.

| biomarker | coefficient | coefficient identifier |
|---|---|---|
| C-reactive protein | 0.025 | b1 |
| carcinoembryonic antigen | 0.501 | b2 |
| beta-2-microglobulin | 1.882 | b3 |
| age | −0.033 | b4 |

The units of measurements of each of the biomarkers are as follows:

TABLE 25

Biomarker units for Example 9, Model 2.

| biomarker | units |
|---|---|
| C-reactive protein | milligrams per liter |
| carcinoembryonic antigen | nanogram per milliliter |
| beta-2-microglobulin | microgram per milliliter |
| age | years |

Accordingly, a risk score for an individual using this model can be determined as follows:

b1*ln(C-reactive protein)+b2*ln(carcinoembryonic antigen)+b3*ln(beta-2-microglobulin)+b4*(age)

where b1 through b4 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.69 (95% CI: 0.65-0.72). This was found to be significantly different than the futility AUC value of 0.5 (p<0.05). As such, it is concluded that the risk score based on the four biomarkers listed in Table 24 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the three blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising twelve variables, was then compared to a model comprising only the nine variables representing traditional risk factors, and evidence for an improvement in risk prediction upon the addition of the three blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into five categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the three biomarkers based on the score plus the nine traditional risk factor variables, and for a model comprising solely the nine established clinical risk factors listed above (without the three biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2):157-72.) The results are as follows:

AUC for three biomarker model plus 9 traditional risk factors: 0.73 (95% confidence interval (CI): 0.69-0.77)

AUC for 9 established risk factors only: 0.68 (95% CI: 0.64-0.72)

p-value for difference in AUC between two models: p<0.001

IDI=5.0% (95% CI: 3.3%-6.8%), p<0.001

Thus, the addition of the three biomarkers, namely, C-reactive protein, carcinoembryonic antigen, and beta-2-microglobulin, to traditional risk factors yields a better set of biomarkers for risk prediction of near term MI than traditional risk factors alone.

EXAMPLE 10

The study population, established risk factors, and putative biomarkers are as described in Example 1. The variables representing putative biomarkers are treated as continuous variables.

Logistic regression models were evaluated to assess the association between baseline variables and incidence of myocardial MI. The model in this example comprises the following five blood plasma analytes, i.e., five biomarkers: alpha-1 antitrypsin, carcinoembryonic antigen, beta-2-microglobulin, apolipoprotein B, and apolipoprotein A1.

Model 1

An unconditional logistic regression model was fitted that included as predictor variables only the five blood plasma analytes, i.e., five biomarkers: alpha-1 antitrypsin, carcinoembryonic antigen, beta-2-microglobulin, apolipoprotein B, and apolipoprotein A1. Using statistical software (R software, version 2.6), the coefficients of each of the five analytes were estimated to be the following:

TABLE 26

Biomarker coefficients for Example 10, Model 1.

| biomarker | coefficient | coefficient identifier |
|---|---|---|
| alpha-1 antitrypsin | 1.340 | b1 |
| carcinoembryonic antigen | 0.496 | b2 |
| beta-2-microglobulin | 1.088 | b3 |
| apolipoprotein B | 0.012 | b4 |
| apolipoprotein A1 | −0.010 | b5 |

The units of measurements of each of the biomarkers are as follows:

TABLE 27

Biomarker units for Example 10, Model 1.

| biomarker | units |
|---|---|
| alpha-1 antitrypsin | micromol |
| carcinoembryonic antigen | nanogram per milliliter |
| beta-2-microglobulin | microgram per milliliter |
| apolipoprotein B | grams per liter |
| apolipoprotein A1 | grams per liter |

Accordingly, a risk score for an individual using this model can be determined as follows:

$$b1*\ln(\text{alpha-1 antitrypsin})+b2*\ln(\text{carcinoembryonic antigen})+b3*\ln(\text{beta-2-microglobulin})+b4*\ln(\text{apolipoprotein B})+b5*\ln(\text{apolipoprotein A1})$$

where b1 through b5 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the five biomarkers. The AUC, and its accompanying 95% confidence interval (CI), was found to be 0.72 (95% CI: 0.68-0.76). This was found to be significantly different than the futility AUC value of 0.5 (p<0.05). As such, it is concluded that the risk score based on the five biomarkers listed in Table 26 is a significant predictor of the risk of near term MI.

Model 2

An unconditional logistic regression model was fitted that included as predictor variables the five blood plasma analytes, i.e., five biomarkers: C-reactive protein, carcinoembryonic antigen, and beta-2-microglobulin, plus age. Using statistical software (R software, version 2.6), the coefficients of each of the five variables were estimated to be the following:

TABLE 28

Biomarker coefficients for Example 10, Model 2.

| biomarker | coefficient | coefficient identifier |
|---|---|---|
| alpha-1 antitrypsin | 1.436 | b1 |
| carcinoembryonic antigen | 0.523 | b2 |
| beta-2-microglobulin | 1.557 | b3 |
| apolipoprotein B | 0.011 | b4 |
| apolipoprotein A1 | −0.009 | b5 |
| age | −0.028 | b6 |

The units of measurements of each of the biomarkers are as follows:

TABLE 29

Biomarker units for Example 10, Model 2.

| biomarker | units |
|---|---|
| alpha-1 antitrypsin | micromol |
| carcinoembryonic antigen | nanogram per milliliter |
| beta-2-microglobulin | microgram per milliliter |
| apolipoprotein B | grams per liter |
| apolipoprotein A1 | grams per liter |
| age | years |

Accordingly, a risk score for an individual using this model can be determined as follows:

$$b1*\ln(\text{alpha-1 antitrypsin})+b2*\ln(\text{carcinoembryonic antigen})+b3*\ln(\text{beta-2-microglobulin})+b4*\ln(\text{apolipoprotein B})+b5*\ln(\text{apolipoprotein A1})+b6*(\text{age})$$

where b1 through b6 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the five biomarkers. The AUC, and its accompanying 95% confidence interval (CI), was found to be 0.73 (95% CI: 0.69-0.77). This was found to be significantly different than the futility AUC value of 0.5 (p<0.05). As such, it is concluded that the risk score based on the six biomarkers listed in Table 28 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the five blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising twelve variables, was then compared to a model comprising only the nine variables representing traditional risk factors, and evidence for an improvement in risk prediction upon the addition of the five blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into five categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the five biomarkers based on the score plus the nine traditional risk factor variables, and for a model comprising solely the nine established clinical risk factors listed above (without the five biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2):157-72.) The results are as follows:

AUC for five biomarker model plus 9 traditional risk factors: 0.75 (95% confidence interval (CI): 0.71-0.78)

AUC for 9 established risk factors only: 0.68 (95% CI: 0.64-0.72)

p-value for difference in AUC between two models: p<0.001

IDI=7.4% (95% CI: 5.3%-9.4%), p<0.001

Thus, the addition of the five biomarkers, namely, alpha-1 antitrypsin, carcinoembryonic antigen, beta-2-microglobulin, apolipoprotein B and apolipoprotein A1, to traditional risk factors yields a better set of biomarkers for risk prediction of near term MI than traditional risk factors alone.

EXAMPLE 11

The study population, established risk factors, and putative biomarkers are as described in Example 1. The variables representing putative biomarkers are treated as continuous variables.

Logistic regression models were evaluated to assess the association between baseline variables and incidence of MI. The model in this example comprises the following six blood plasma analytes, i.e., six biomarkers: apolipoprotein B, apolipoprotein A1, N-terminal B-type natriuretic peptide (NT-proBNP), carcinoembryonic antigen, beta-2-microglobulin, and C-reactive protein.

Model 1

An unconditional logistic regression model was fitted that included as predictor variables only the six blood plasma analytes, i.e., six biomarkers: apolipoprotein B, apolipoprotein A1, N-terminal B-type natriuretic peptide (NT-proBNP), carcinoembryonic antigen, beta-2-microglobulin, and C-reactive protein. Using statistical software (R software, version 2.6), the coefficients of each of the six analytes were estimated to be the following:

TABLE 30

Biomarker coefficients for Example 11, Model 1.

| biomarker | coefficient | coefficient identifier |
| --- | --- | --- |
| C-reactive protein | 0.020 | b1 |
| carcinoembryonic antigen | 0.498 | b2 |
| beta-2-microglobulin | 0.912 | b3 |
| apolipoprotein B | 0.012 | b4 |
| apolipoprotein A1 | −0.010 | b5 |
| NT-proBNP | 0.158 | b6 |

The units of measurements of each of the biomarkers are as follows:

TABLE 31

Biomarker units for Example 11, Model 1.

| biomarker | units |
| --- | --- |
| C-reactive protein | milligrams per liter |
| carcinoembryonic antigen | nanogram per milliliter |
| beta-2-microglobulin | microgram per milliliter |
| apolipoprotein B | grams per liter |
| apolipoprotein A1 | grams per liter |
| NT-proBNP | picograms per liter |

Accordingly, a risk score for an individual using this model can be determined as follows:

b1*ln(C-reactive protein)+b2*ln(carcinoembryonic antigen)+b3*ln(beta-2-microglobulin)+b4*ln(apolipoprotein B)+b5*ln(apolipoprotein A1)+b6*ln(NT-proBNP)

where b1 through b6 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the six biomarkers. The AUC, and its accompanying 95% confidence interval (CI), was found to be 0.71 (95% CI: 0.67-0.75). This was found to be significantly different than the futility AUC value of 0.5 (p<0.05). As such, it is concluded that the risk score based on the six biomarkers listed in Table 30 is a significant predictor of the risk of near term MI.

Model 2

An unconditional logistic regression model was fitted that included as predictor variables the six blood plasma analytes, i.e., six biomarkers: apolipoprotein B, apolipoprotein A1, N-terminal B-type natriuretic peptide (NT-proBNP), carcinoembryonic antigen, beta-2-microglobulin, and C-reactive protein, plus age. Using statistical software (R software, version 2.6), the coefficients of each of the six variables were estimated to be the following:

TABLE 32

Biomarker coefficients for Example 11, Model 2.

| biomarker | coefficient | coefficient identifier |
| --- | --- | --- |
| C-reactive protein | 0.018 | b1 |
| carcinoembryonic antigen | 0.531 | b2 |

TABLE 32-continued

Biomarker coefficients for Example 11, Model 2.

| biomarker | coefficient | coefficient identifier |
|---|---|---|
| beta-2-microglobulin | 1.419 | b3 |
| apolipoprotein B | 0.011 | b4 |
| apolipoprotein A1 | −0.009 | b5 |
| NT-proBNP | 0.237 | b6 |
| age | −0.037 | b7 |

The units of measurements of each of the biomarkers are as follows:

TABLE 33

Biomarker units for Example 11, Model 2.

| biomarker | units |
|---|---|
| C-reactive protein | milligrams per liter |
| carcinoembryonic antigen | nanogram per milliliter |
| beta-2-microglobulin | microgram per milliliter |
| apolipoprotein B | grams per liter |
| apolipoprotein A1 | grams per liter |
| NT-proBNP | picograms per liter |
| age | years |

Accordingly, a risk score for an individual using this model can be determined as follows:

b1*ln(C-reactive protein)+b2*ln(carcinoembryonic antigen)+b3*ln(beta-2-microglobulin)+b4*ln(apolipoprotein B)+b5*ln(apolipoprotein A1)+b6*ln(NT-proBNP)+b7*(age)

where b1 through b7 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the six biomarkers. The AUC, and its accompanying 95% confidence interval (CI), was found to be 0.73 (95% CI: 0.69-0.76). This was found to be significantly different than the futility AUC value of 0.5 (p<0.05). As such, it is concluded that the risk score based on the seven biomarkers listed in table 32 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the six blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising twelve variables, was then compared to a model comprising only the nine variables representing traditional risk factors, and evidence for an improvement in risk prediction upon the addition of the six blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into six categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the six biomarkers based on the score plus the nine traditional risk factor variables, and for a model comprising solely the nine established clinical risk factors listed above (without the six biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. *Stat. Med.* 27(2):157-72 (2008)). The results are as follows:

AUC for six biomarker model plus 9 traditional risk factors: 0.75 (95% confidence interval (CI): 0.71-0.79)

AUC for 9 established risk factors only: 0.68 (95% CI: 0.64-0.72)

p-value for difference in AUC between two models: p<0.001

IDI=7.3% (95% CI: 5.3%-9.4%), p<0.001

Thus, the addition of the six biomarkers, namely, apolipoprotein B, apolipoprotein A1, N-terminal B-type natriuretic peptide, carcinoembryonic antigen, beta-2-microglobulin, and C-reactive protein, to traditional risk factors yields a better set of biomarkers for risk prediction of near term MI than traditional risk factors alone.

EXAMPLE 12

The study population, established risk factors, and putative biomarkers are as described in Example 1. The variables representing putative biomarkers are treated as continuous variables.

Logistic regression models were evaluated to assess the association between baseline variables and incidence of MI. The model in this example comprises the following three blood plasma analytes, i.e., three biomarkers: carcinoembryonic antigen, beta-2-microglobulin, and N-terminal B-type natriuretic peptide (NT-proBNP).

Model 1

An unconditional logistic regression model was fitted that included as predictor variables only the three blood plasma analytes, i.e., three biomarkers: carcinoembryonic antigen, beta-2-microglobulin, and N-terminal B-type natriuretic peptide (NT-proBNP). Using statistical software (R software, version 2.6), the coefficients of each of the three analytes were estimated to be the following:

TABLE 34

Biomarker coefficients for Example 12, Model 1.

| biomarker | coefficient | coefficient identifier |
|---|---|---|
| carcinoembryonic antigen | 0.457 | b1 |
| beta-2-microglobulin | 1.209 | b2 |
| NT-proBNP | 0.080 | b3 |

The units of measurements of each biomarkers are as follows:

TABLE 35

Biomarker units for Example 12, Model 1.

| biomarker | units |
|---|---|
| carcinoembryonic antigen | nanogram per milliliter |
| beta-2-microglobulin | microgram per milliliter |
| NT-proBNP | picograms per liter |

Accordingly, a risk score for an individual using this model can be determined as follows:

$$b1*\ln(\text{carcinoembryonic antigen})+b2*\ln(\text{beta-2-microglobulin})+b3*\ln(\text{NT-proBNP})$$

where b1 through b3 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.66 (95% CI: 0.61-0.70). This was found to be significantly different than the futility AUC value of 0.5 (p<0.05). As such, it is concluded that the risk score based on the three biomarkers listed in Table 34 is a significant predictor of the risk of near term MI.

Model 2

An unconditional logistic regression model was fitted that included as predictor variables the three blood plasma analytes, i.e., three biomarkers: carcinoembryonic antigen, beta-2-microglobulin, and N-terminal B-type natriuretic peptide (NT-proBNP), plus age. Using statistical software (R software, version 2.6), the coefficients of each of the three variables were estimated to be the following:

TABLE 36

Biomarker coefficients for Example 12, Model 2.

| biomarker | coefficient | coefficient identifier |
|---|---|---|
| carcinoembryonic antigen | 0.510 | b1 |
| beta-2-microglobulin | 1.864 | b2 |
| NT-proBNP | 0.181 | b3 |
| age | −0.045 | b4 |

The units of measurements of each biomarkers are as follows:

TABLE 37

Biomarker units for Example 12, Model 2.

| biomarker | units |
|---|---|
| carcinoembryonic antigen | nanogram per milliliter |
| beta-2-microglobulin | microgram per milliliter |
| NT-proBNP | picograms per liter |
| age | years |

Accordingly, a risk score for an individual using this model can be determined as follows:

$$b1*\ln(\text{carcinoembryonic antigen})+b2*\ln(\text{beta-2-microglobulin})+b3*\ln(\text{NT-proBNP})+b4*(\text{age})$$

where b1 through b4 are the coefficients listed in the table above, and ln(x) indicates the logarithmically transformed value of x using base e. The score from this model was calculated for each individual. It will be understood from one skilled in the art that an additional constant value, also known as an 'intercept term', may be added to a risk score calculated in such a manner. A higher risk score represents an increased likelihood of MI within 4 years of testing.

The area under the receiver-operating characteristic ('ROC') curve, 'AUC', was calculated based on the risk score equation above derived from the three biomarkers. The AUC, and its accompanying 95% confidence interval (CI), was found to be 0.70 (95% CI: 0.66-0.74). This was found to be significantly different than the futility AUC value of 0.5 (p<0.05). As such, it is concluded that the risk score based on the four biomarkers listed in Table 36 is a significant predictor of the risk of near term MI.

Added Predictive Value

In order to determine whether the addition of this score, derived from measurements of the plasma analytes, added predictive value for the occurrence of MI beyond the simple evaluation of traditional risk factors, the following exercise was also conducted. A logistic regression model comprising the three blood plasma analyte variables as well as nine additional variables representing traditional risk factors (see, e.g., Wilson P W, D'Agostino R B, Levy D, Belanger A M, Silbershatz H, Kannel W B. Prediction of coronary heart disease using risk factor categories. *Circulation* 97:1837-47 (1998)) was evaluated. This model, comprising twelve variables, was then compared to a model comprising only the nine variables representing traditional risk factors, and evidence for an improvement in risk prediction upon the addition of the three blood plasma biomarkers was sought. The nine traditional risk factors that were considered represent medical community consensus, and are as follows (all evaluated at time of blood collection): (i) smoking (never, former smoker, or current smoker), (ii) blood pressure (categorized into three categories as follows: blood pressure: <120/80 mmHg, ≥120/80&<130/85 mmHg, ≥130/85&<140/90 mmHg, ≥140/90&<160/100 mmHg, and ≥160/100 mmHg or use of antihypertensive therapy, where the numerators are systolic blood pressure and denominators are diastolic blood pressure), (iii) total cholesterol (treated as an untransformed continuous variable), (iv) high density lipoprotein (HDL) cholesterol (treated as an untransformed continuous variable), (v) diabetes status (yes/no), (vi) age (treated as an untransformed continuous variable), (vii) gender, (viii) statin therapy use (yes/no), (ix) year of blood collection (2001, 2002, 2003, 2004, 2005, or 2006).

Subsequently, the area under the ROC curve ('AUC') was calculated for the model comprising the three biomarkers based on the score plus the nine traditional risk factor variables, and for a model comprising solely the nine established clinical risk factors listed above (without the three biomarkers). In addition, the integrated discrimination improvement ('IDI') was calculated comparing these two models (per Pencina M J, D'Agostino R B Sr, D'Agostino R B Jr, Vasan R S. Evaluating the added predictive ability of a new marker: from area under the ROC curve to reclassification and beyond. Stat Med 2008 Jan. 30; 27(2):157-72.) The results are as follows:

AUC for three biomarker model plus 9 traditional risk factors: 0.75 (95% confidence interval (CI): 0.71-0.78)
AUC for 9 established risk factors only: 0.68 (95% CI: 0.64-0.72)
p-value for difference in AUC between two models: p<0.001
IDI=6.7% (95% CI: 4.7%-8.6%), p<0.001

Thus, the addition of the three biomarkers, namely, carcinoembryonic antigen, beta-2-microglobulin, and N-terminal B-type natriuretic peptide, to traditional risk factors yields a better set of biomarkers for risk prediction of near term MI than traditional risk factors alone.

It should be understood that the use of headings and sections in the application is not meant to limit the present teachings; each section can apply to any aspect, embodiment, or feature of the present teachings.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of embodiments of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value, unless otherwise indicated or inferred.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the present teachings as if each value were specifically enumerated herein. In addition, smaller ranges between and including the upper and lower limits of a given range are contemplated and encompassed within the present teachings. The listing of exemplary values or ranges is not a disclaimer of other values or ranges between and including the upper and lower limits of a given range.

Variations, modifications, and other implementations of what is described herein will occur to those of ordinary skill in the art without departing from the spirit and the essential characteristics of the invention. Accordingly, the scope of the present teachings is to be defined not by the preceding illustrative description but instead by the following claims, and all changes that come within the meaning and range of equivalency of the claims are intended to be embraced therein.

What is claimed is:

1. A method of diagnosing the risk of a future myocardial infarction in an individual, the method comprising:
measuring the level of each biomarker of a set of biomarkers in a sample from an individual, wherein each biomarker of the set of biomarkers is measured using a respective antibody that specifically measures the biomarker and the set of biomarkers comprises:
(i) carcinoembryonic antigen, beta-2 microglobulin and transferrin; and
(ii) at least one of N-terminal pro B-type natriuretic peptide, alpha-1 antitrypsin, and C-reactive protein;
calculating a risk score for the individual by weighting the measured levels of the biomarkers, wherein calculating a risk score comprises:
transforming logarithmically the measured levels of the biomarkers to generate a transformed value for each measured biomarker;
multiplying the transformed value of each biomarker by a biomarker constant to generate a multiplied value for each biomarker; and
summing the multiplied value of each biomarker to generate the risk score; and
using the risk score to identify a likelihood that the individual will experience a myocardial infarction in the future.

2. The method of claim 1, wherein the set of biomarkers comprises N-terminal pro B-type natriuretic peptide.

3. The method of claim 1, wherein the set of biomarkers comprises alpha-1 antitrypsin.

4. The method of claim 3, wherein the set of biomarkers comprises N-terminal pro B-type natriuretic peptide.

5. The method of claim 3, wherein the set of biomarkers further comprises apolipoprotein A1 and apolipoprotein B.

6. The method of claim 5, wherein the set of biomarkers further comprises alpha fetoprotein.

7. The method of claim 6, wherein the set of biomarkers further comprises vascular endothelial growth factor.

8. The method of claim 1, wherein the set of biomarkers comprises C-reactive protein.

9. The method of claim 8, wherein the set of biomarkers further comprises N-terminal pro B-type natriuretic peptide, apolipoprotein A1, and apolipoprotein B.

10. The method of claim 1, comprising the step of transmitting, displaying, storing, or printing; or outputting to a user interface device, a computer readable storage medium, a local computer system or a remote computer system, information related to the likelihood of myocardial infarction in the individual.

11. The method of claim 10, wherein the information is the risk score or an equivalent thereof.

12. The method of claim 1, comprising recommending, authorizing, or administering treatment if the individual is identified as having an increased likelihood of a future myocardial infarction.

13. The method of claim 1, comprising identifying the individual as having an increased likelihood of having a future myocardial infarction event if the risk score is greater than a reference risk score, and identifying the individual as having a decreased likelihood of having a future myocardial infarction event if the risk score is less than the reference risk score.

14. The method of claim 13, wherein the reference risk score is a standard or a threshold.

15. The method of claim 1, wherein the calculating is performed using a computer adapted to calculate a risk score.

16. The method of claim 1, wherein the sample comprises blood.

17. The method of claim 1, wherein the individual is human.

18. The method of claim 1, wherein the risk of a future myocardial infarction is a near-term risk.

19. The method of claim 1, wherein the risk score comprises a weighted metric of the individual's age.

20. The method of claim 1 wherein the risk score comprises a weighted metric of one or more clinical risk factors for the individual, wherein the one or more clinical risk factors are selected from the group consisting of smoking status, diabetes mellitus, family history of premature myocardial infarction, body mass index, physical activity, non-fasting total cholesterol, HDL cholesterol, LDL cholesterol, and triglycerides.

21. A method of diagnosing the risk of a future myocardial infarction in a human, the method comprising:
    measuring the level of each biomarker of a set of biomarkers in a sample from a human, wherein each biomarker of the set of biomarkers is measured using a respective antibody that specifically measures the biomarker and the set of biomarkers comprises carcinoembryonic antigen, beta-2 microglobulin, transferrin and N-terminal pro B-type natriuretic peptide;
    calculating a risk score for the human by weighting the measured levels of the biomarkers, wherein calculating a risk score comprises:
    transforming logarithmically measured levels of the biomarkers to generate a transformed value for the measured biomarkers;
    multiplying the transformed value of the biomarkers by a biomarker constant to generate a multiplied value for the biomarkers; and
    summing the multiplied values of the biomarkers for the risk score; and
    using the risk score to identify a likelihood that the human will experience a myocardial infarction in the future.

22. The method of claim 21, wherein the set of biomarkers further comprises C-reactive protein.

23. The method of claim 22, wherein the set of biomarkers further comprises apolipoprotein A1.

24. The method of claim 23, wherein the set of biomarkers further comprises apolipoprotein B.

25. A method of diagnosing the risk of a future myocardial infarction in a human, the method comprising:
    measuring the level of each biomarker of a set of biomarkers in a sample from a human, wherein each biomarker of the set of biomarkers is measured using a respective antibody that specifically measures the biomarker and the set of biomarkers comprises carcinoembryonic antigen, beta-2 microglobulin, N-terminal pro B type natriuretic peptide, C-reactive protein, apolipoprotein A1, apolipoprotein B, and transferrin;
    calculating a risk score for the human by weighing the measured levels of the biomarkers and comprising:
    transforming logarithmically measured levels of the biomarkers to generate a transformed value for the measured biomarkers;
    multiplying the transformed value of the biomarkers by a biomarker constant to generate a multiplied value for the biomarkers; and
    summing the multiplied values of the biomarkers for the risk score; and
    using the risk score to identify a likelihood that the human will experience a myocardial infarction in the future.

26. The method of claim 25, comprising recommending, authorizing, or administering treatment if the human is identified as having an increased likelihood of a future myocardial infarction.

27. The method of claim 25, wherein the calculating is performed using a computer adapted to calculate a risk score.

28. The method of claim 25, wherein the risk of a future myocardial infarction is a near-term risk.

* * * * *